United States Patent
Wilson et al.

(10) Patent No.: US 9,404,102 B2
(45) Date of Patent: *Aug. 2, 2016

(54) TREATMENT OF DISEASE CONDITIONS VIA ADMINISTRATION OF DNA REPAIR ENZYME

(71) Applicant: University of South Alabama, Mobile, AL (US)

(72) Inventors: Glenn Wilson, Daphne, AL (US); Susan Ledoux, Mobile, AL (US); Mikhail Alexeyev, Mobile, AL (US); Inna Shokolenko, Mobile, AL (US); Mark N. Gillespie, Daphne, AL (US)

(73) Assignee: University of South Alabama, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,458

(22) Filed: Oct. 20, 2014

(65) Prior Publication Data

US 2015/0118217 A1 Apr. 30, 2015

Related U.S. Application Data

(63) Continuation of application No. 12/866,540, filed as application No. PCT/US2009/000889 on Feb. 9, 2009, now Pat. No. 8,865,160.

(60) Provisional application No. 61/065,044, filed on Feb. 8, 2008.

(51) Int. Cl.

| | | |
|---|---|---|
| *C12N 9/24* | (2006.01) | |
| *C07K 14/435* | (2006.01) | |
| *C07K 14/005* | (2006.01) | |
| *C12N 9/22* | (2006.01) | |
| *C12N 7/00* | (2006.01) | |
| *A61K 47/48* | (2006.01) | |
| *C12N 9/88* | (2006.01) | |
| *A61K 38/00* | (2006.01) | |

(52) U.S. Cl.
CPC ........ *C12N 9/2497* (2013.01); *A61K 47/48238* (2013.01); *C07K 14/005* (2013.01); *C07K 14/435* (2013.01); *C12N 7/00* (2013.01); *C12N 9/22* (2013.01); *C12N 9/88* (2013.01); *C12Y 302/02023* (2013.01); *C12Y 402/99018* (2013.01); *A61K 38/00* (2013.01); *C07K 2319/07* (2013.01); *C07K 2319/10* (2013.01); *C12N 2740/16371* (2013.01); *C12Y 301/21005* (2013.01)

(58) Field of Classification Search
CPC ............ A61K 38/00; A61K 47/48238; C07K 14/005; C07K 14/435; C07K 2319/07; C07K 2319/10; C12N 2740/16371; C12N 7/00; C12N 9/22; C12N 9/2497; C12N 9/88; C12Y 301/21005; C12Y 302/02023; C12Y 402/99

See application file for complete search history.

(56) References Cited

U.S. PATENT DOCUMENTS

2005/0255093 A1   11/2005   Shone et al.

FOREIGN PATENT DOCUMENTS

| WO | 2005042560 A2 | 5/2005 |
| WO | 2009097568 A1 | 8/2009 |
| WO | 2009098682 A2 | 8/2009 |

OTHER PUBLICATIONS

Toshiya Endo, Functions of outer membrane receptors in mitochondrial protein import, Biochimica et Biophysica Acta 1592 (2002) 3-14.*
Abu-Amer, Y., S. Dowdy, F. Ross, J. Clohisy, and S. Teitelbaum, TAT fusion proteins containing tyrosine 42-deleted IkappaBalpha arrest osteoclastogenesis. J Biol Chem, 2001. 276: p. 30499-30503.
Attardi, G. and S. G, Biogenesis of mitochondria. Ann Rev Cell Biol, 1988. 4: p. 289-333.
Bogenhagen, D., K Pinz, and R. Perez-Jannotti, Enzymology of mitochondrial base excision repair. Prog Nucleic Acid Res Mol Biol, 2001. 68: p. 257-271.
Caron, N., Y. Torrente, G. Camirand, M. Bujold, P. Chapdelaine, K. Leriche, N. Bresolin, and J. Tremblay, Intracellualr delivery of a Tat-eGFP fusion protein into muscle cells. Mol Ther, 2001. 3: p. 310-318.
Chellaiah, M., N. Soga, S. Swanson, S. McAllister, U. Alvarez, D. Wang, S. Dowdy, and K. Hruska, Rho-A is critical for osteoclast podosome organization, motility, and bone resorption. J Biol Chem, 2000. 275: p. 11993-12002.
Chinnery, P. and D. Turnbull, Mitochondrial DNA and disease. Lancet, 1999. 354: p. 17-21.
Dobson A W et al: American Journal of Physiology Lung Cellular and Molecular Physiology, 283(1); L205-L210 (2002), XP008116893.
Dobson, A., Y. Xu, M. Kelley, S. LeDoux, and G. Wilson, Enhanced mtDNA repair and cellular survival following oxidative stress by targeting the hOGG repair enzyme to mitochondria. J Biol Chem, 2000. 275: p. 37518-37523.
Doetsch, P. and R. Cunningham, the enzymology of apurinic/apyrimidinic endonucleases. Mutation Res, 1990. 236: p. 173-201.
Donath, M. and P. Halban, Decreased beta-cell mass in diabetes: significance, mechanisms and therapeutic implications. Diabetologia, 2004. 47: p. 581-589.
Driggers, W., S. LeDoux, and G. Wilson, Repair of oxidative damage within the mitochondrial DNA of RINr 38 cells. J Biol Chem, 1993. 268: p. 22042-22045.

(Continued)

*Primary Examiner* — James H Alstrum Acevedo
*Assistant Examiner* — Erinne Dabkowski
(74) *Attorney, Agent, or Firm* — Lerner, David, Littenberg, Krumholz & Mentlik, LLP

(57) ABSTRACT

The present invention is directed to compositions and methods of preserving viability of islets of Langerhans for transplantation, and treating various disease and other abnormal or pathological conditions, including inflammatory bowel disease, ischemic heart disease, acute lung injury, acute respiratory distress syndrome and radiation-induced brain injury, with DNA repair enzymes that are directed to the mitochondria.

21 Claims, 14 Drawing Sheets

(56) References Cited

OTHER PUBLICATIONS

Druzhyna, N., B. Hollensworth, M. Kelley, G. Wilson, and S. LeDoux, Targeting human 8-oxoguanine glycosylase to mitochondria of oligodendrocytes protects against menadione-induced oxidative stress. Glia, 2003. 42: p. 370-378.

Eizirik, D. and T. Mandrup-Poulsen, A choice of death—the signal-transduction of immune-mediated beta-cell apoptosis. Diabetologia, 2001. 44: p. 2115-2133.

Elliott, G. and P. O'Hare, Intercellular trafficking and protein delivery by a herpesvirus structural protein. Cell, 1997. 88: p. 223-233.

Embury, J., D. Klein, A. Pileggi, M. Ribeiro, S. Jayaraman, R. Molano, C. Fraker, N. Kenyon, C. Ricordi, L. Inverardi, and R. Pastori, Proteins linked to a protein transduction domain efficiently transduce pancreatic islets. Diabetes, 2001. 50: p. 1706-1713.

Ezhevsky, S., A. Ho, M. Becher-Hapak, P. Davis, and S. Dowdy, Differential regulation of retinoblastoma tumor suppressor protein by G(1) cyclin-dependent kinase complexes in vivo. Mol Cell Biol, 2001. 21: p. 4773-4784.

Ezhevsky, S., H. Nagahara, A. Vocero-Akbani, D. Gius, M. Wei, and S. Dowdy, Hypo-phosphorylation of the retinoblastoma protein (pRb) by cyclin D:Cdk4/6 complexes results in active pRb. Proc Natl Acad Sci USA, 1997. 94: p. 10699-10704.

Ferri, K. and G. Kroemer, Mitochondria—the suicide organelles. Bioessays, 2001. 23: p. 111-115.

Frei, B., K. Winterhalter, and C. Richter, Menadione- (2-methyl-1,4-naphthoquinone-) dependent enzymatic redox cycling and calcium release by mitochondria. Biochemistry, 1986. 25: p. 4438-4443.

Frenkel, A. and C. Pabo, Cellular uptake of the tat protein from human immunodeficiency virus. Cell, 1988. 55: p. 1189-1193.

Futaki, S., T. Suzuki, W. Ohashi, T. Yagami, S. Tanaka, K. Ueda, and Y. Sugiura, Arginine-rich peptides. an abundant source of membrane-permiable peptides having potential as carriers for intracellular protein delivery. J Biol Chem, 2001. 276: p. 5836-5840.

Gaglia, J., A. Shapiro, and G. Weir, Islet transplatation: Progress and challenge. Archives of Medical Research, 2005. 36: p. 273-280.

Green, M. and P. Loewenstein, Autonomous functional domains of chemically synthesized human immunodeficiency virus tat trans-activator protein. Cell, 1988. 55: p. 1179-1188.

Grishko, V., L. Rachek, S. Musiyenko, S. LeDoux, and G. Wilson, Involvement of mtDNA damage in free fatty acid-induced apoptosis. Free Radic Biol Med, 2005. 38(6): p. 755-762.

Grossman, L. and E. Shoubridge, Mitochondrial genetics and human disease. BioEssays, 1996. 18: p. 983-991.

Grossman, L., Mitochondrial mutations and human disease. Environ Mol Mutagen, 1995. 25 (Suppl. 26): p. 30-37.

Hall, D., J. Cui, M. Bates, B. Stout, L. Koenderman, P. Coffer, and P. Bertics, Transduction of a dominant-negative H-Ras into human eosinophils attenuates extracellular signal-regulated kinase activation and interleukin-5-mediated cell viability. Blood, 2001. 98: p. 2014-2021.

Hatefi, Y., The mitochondrial electron transport and oxidative phosporylation system. Ann Rev Biochem, 1985. 54: p. 1015-1069.

Ho, A., S. Schwarze, S. Mermelstein, G. Waksman, and S. Dowdy, Synthetic protein transduction domains: enhanced protein transduction potential in vitro and in vivo. Cancer Res, 2001. 61: p. 474-477.

Hollensworth, B., C. Shen, J. Sim, D. Spitz, G. Wilson, and S. Ledoux, Glial cell type-specific responses to menadione-induced oxidative stress. Free Radical Biology and Medicine, 2000. 28: p. 1161-1174.

International Search Report, PCT/US2009/000889, Feb. 5, 2010.

Joliot, A., A. Triller, M. Volovitch, C. Pernelle, and A. Prochiantz, Alpha-2,8-polysialic acid is the neuronal surface receptor of antennapedia homeobox peptide. New Biol, 1991. 3: p. 1121-1134.

Joliot, A., C. Pernelle, H. Deagostini-Bazin, and A. Prochiantz, Atennapedia homeobox peptide regulates neural morphogenesis. Proc Natl Acad Sci USA, 1991. 88: p. 1864-1868.

Josa, A., S. Susin, E. Daugas, W. Stanford, S. Cho, C. Li, A. Sasaki, H. Ella, L. Chang, L. Ravagnan, K. Ferri, N. Zanami, A. Wakeham, R. Hakem, H. Yoshida, Y. Kong, T. Mak, J. Zuniga-Pflucker, G. Kroemer, and J. Penninger, Essential role of the mitochondrial apoptosis-inducing factor in programmed cell death. Nature, 2001. 410: p. 549-554.

Kharroubi, I., L. Ladriere, A. Cardozo, Z. Dogusan, M. Cnop, and D. Eizirik, Free Fatty Acids and Cytokines Induce Pancreatic beta-cell apoptosis by different mechanisms: Role of nuclear factor-kappabeta and endoplasmic reticulum stress. Endocrinology, 2004. 145: p. 5087-5098.

Klein, D., M. Ribeiro, V. Mendoza, S. Jayaraman, N. Kenyon, A. Pileggi, R. Molano, L. Inverardi, C. Ricordi, and R. Pastori, Delivery of BCL-XL or its BH4 domain by protein transduction inhibits apoptosis in human islets. Biochem Biophys Res Comm, 2004. 323: p. 473-478.

Klekotka, P., S. Santoro, A. Ho, S. Dowdy, and M. Zutter, Mammary epithelial cell-cycle progression via the alpha(2) beta(1) integrin: unique and synergistic roles of the alpha(2) cytoplasmic domain. Am J Pathol, 2001. 159: p. 983-992.

Kujoth, G., A. Hiona, T. Pugh, S. Someya, K. Panzer, S. Wiohlgemuth, T. Hofer, A. Seo, R. Sullivan, W. Jobling, J. Morrow, H. Remmen, J. Sedivy, T. Yamasoba, M. Tanokura, R. Weindruch, C. Leeuwenburgh, and T. Prolla, Mitochondrial DNA mutations, oxidative stress, and apoptosis in mammalian aging. Science, 2005. 309: p. 481-484.

Larsson, N.-G. and D. Clayton, Molecular genetic aspects of human mitochondrial disorders. Annu Rev Genetics, 1995. 29: p. 151-178.

Larsson, N.-G. and R. Luft, Revolution in mitochondrial medicine. FEBS Lett, 1999. 455: p. 199-202.

Le Roux, I., A. Joliot, E. Bloch-Gallego, A. Prochiantz, and M. Volovitch, Neurotrophic activity of the Antennapedia homeodomain depends on its specific DNA-binding properties. Proc Natl Acad Sci USA, 1993. 90: p. 9120-9124.

LeDoux, S. and G. Wilson, Base excision repair of mitochondrial DNA damage in mammalian cells. Prog Nucleic Acid Res Mol Biol, 2001. 68: p. 273-284.

LeDoux, S., N. Patton, J. Nelson, V. Bohr, and G. Wilson, Preferential DNA repair of alkali-labile sites within the active insulin gene. J Biol Chem, 1990. 265(25): p. 14875-14880.

LeDoux, S., S. Woodley, N. Patton, and G. Wilson, Mechanisms of nitrosourea-induced beta cell damage: Alterations in DNA. Diabetes, 1986. 35: p. 866-872.

Li, H., Z. Yao, B. Degenhardt, G. Teper, and V. Papadopoulos, Cholesterol binding at the cholesterol recognition/interation amino acid consensus (CRAC) of the peripheral-type benzodiazepine receptor and inhibition of steroidogenesis by an HIV TAT-CRAC peptide. Proc Natl Acad Sci USA, 2001. 98: p. 1267-1272.

Liadis, N., K. Murakami, M. Eweida, A. Elford, L. Sheu, H. Gaisano, R. Hakem, P. Ohashi, and M. Woo, Caspase-3-dependent beta cell apoptosis in the initiation of autoimmune diabetes mellitus. Mol CelL Biol, 2005. 25: p. 3620-3629.

Lissy, N., P. Davis, M. Irwin, W. Kaelin, and S. Dowdy, A common E2F-1 and p73 pathway mediates cell death induced by TCR activation. Nature, 2000. 407: p. 642-645.

Luft, R. and B. Landau, Mitochondrial medicine. J Internal Med, 1995. 238: p. 405-421.

Maestre, I., J. Jordan, S. Calvo, J. Reig, V. Cena, B. Soria, I.M. Prentk, and E. Roche, Mitochondrial dysfunction is involved in apoptosis induced by serum withdrawal and fatty acids in the beta-cell line INS-1. Endocrinology, 2003. 144: p. 335-345.

Mandrup-Poulsen, T., Apoptotic signal transduction pathways in diabetes. Biochem Pharmacol, 2003. 66: p. 1433-1440.

Dizdaroglu, M., Chemical determination of free radical-induced damage to DNA. Free Radic Biol Med, 1991. 10: p. 225-242.

Jacobs, H. and I. Holt, The mitochondrial genetic system, ed. K. Singh. 1998: Springer. pp. 43-83.

LeDoux, S., G. Wilson, E. Beecham, T. Stevsner, K. Wassermann, and V. Bohr, Repair of mitochondrial DNA after various types of DNA damage in Chinese hamster ovary cells. Carcinogenesis, 1992. 13(11): p. 1967-1973.

Wallace, D., Diseases of the mitochondrial DNA. Annu Rev Biochem, 1992. 61: p. 1175-1212.

(56) References Cited

OTHER PUBLICATIONS

Mendoza, V., D. Klein, H. Ichii, M. Ribeiro, C. Ricordi, T. Hankein, T. Burmester, and R. Pastori, Protection of islets in culture by delivery of oxygen binding neuroglobin via protein transduction. Transplant Proc, 2005. 37: p. 237-240.
Michelakis, Circulation, 117; 2431-2434 (2008).
Nagahara, H., A. Vocero-Akbani, E. Snyder, A. Ho, D. Latham, N. Lissy, M. Becher-Hapak, S. Ezhevsky, and S. Dowdy, Transduction of full-length TAT fusion proteins into mammalian cells: TAT-p27Kip1 induces cell migration. Nat Med, 1998. 4: p. 1449-1452.
Nelson, J., S. LeDoux, and G. Wilson, Repair of O6-methylguanine in rat pancreatic beta cells following exposure to N-methyl-N-nitrosourea. Diabetes, 1993. 42: p. 1187-1194.
Noguchi, H., Y. Nakai, S. Matsumoto, M. Kawaguchi, M. Ueda, T. Okitsu, Y. Iwanaga, Y. Yonekawa, H. Nagata, K. Minami, Y. Masui, S. Futaki, and K. Tanaka, Cell permiable peptide of JNK inhibitor prevents islet apoptosis immediately after isolation and improves islet graft function. Am J Transplant, 2005. 5: p. 1848-1855.
Penta, J., F. Johnson, J. Wachsman, and W. Cope, Mitochondrial DNA in human malignancy. Mutation Res, 2001. 488: p. 119-133.
Pettepher, C., S. LeDoux, V. Bohr, and G. Wilson, Repair of alkali label sites within the mitochondrial DNA of RINr 38 cells after exposure to the nitrosourea streptozotocin. J Biol Chem, 1991. 266: p. 3113-3117.
Rachek Lyudmila I et al: Diabetes, 55(4); 1022-1028 (Apr. 2006).
Rachek, L., N. Thornley, V. Grishko, S. LeDoux, and G. Wilson, Protection of INS-1 cells from free fatty acid-induced apoptosis by targeting hOGG1 to mitochondria. Diabetes, 2006. 55: p. 1022-1028.
Rachek, L., V. Grishko, M. Alexeyev, V. Pastukh, S. LeDoux, and G. Wilson, Endonuclease III and endonuclease VIII conditionally targeted into mitochondria enhance mitochondrial DNA repair and cell survival following oxidative stress. Nucleic Acids Res., 2004. 32(10): p. 3240-3247.
Rachek, L., V. Grishko, S. LeDoux, and G. Wilson, Protection against free fatty acid-induced apoptosis in beta cells by targeting a recombinant DNA repair enzyme to mitochondria. Diabetes, 2005. 54: p. 317A.
Rachek, L., V. Grishko, S. LeDoux, and G. Wilson, Role of nitric oxide-induced mtDNA damage in mitochondrial dysfunction and apoptosis. Free Radic Biol Med, 2006. 40: p. 754-762.
Rachek, L., V. Grishko, S. Musiyenko, M. Kelley, S. LeDoux, and G. Wilson, Conditional targeting of the DNA repair enzyme hOGG1 into mitochondria. J Biol Chem, 2002. 277: p. 44932-44937.
Ribeiro, M., D. Klein, A. Pileggi, R. Molano, C. Fraker, C. Ricordi, L. Inverardi, and R. Pastori, Heme oxygenase-1 fused to TAT peptide transduces and protects pancreatic beta-cells. Biochim Biophys Res Comm, 2003. 305: p. 876-881.
Robinson, B., Human complex I deficiency: clinical spectrum and involvement of oxygen free radicals in the pathogenecity of the defect. Biochim Biophys Acta, 1998. 1364271-286.
Schwarze, S., A. Ho, A. Vocero-Akbani, and S. Dowdy, In vivo protein transduction: delivery of a biologically active protein into the mouse. Science, 1999. 285: p. 1569-1572.
Schwarze, S., K. Hruska, and S. Dowdy, Protein transduction: unrestricted delivery into cells? Trends Cell Biol, 2000. 10: p. 290-295.
Shimabukuro, M., M. Ohneda, L. Y, and U. RH, Role of nitric oxide in obesity-induced beta cell disease. J Clin Invest, 1997. 100: p. 290-295.
Shokolenko I N et al: Advances in Biochemistry in Health and Disease Springer, 233 Spring Street, New York, NV 10013, Uniied States Series Advances in Biochemistry in Health and Disease, 2007, pp. 323-347, XP008116872.
Shokolenko I N et al; DNA Repair, Elsevier, Amsterdam, ML, 4(4); 511-518 4 (Apr. 4, 2005).
Shokolenko, I., M. Alexeyev, F. Robertson, S. LeDoux, and G. Wilson, The expression of Exonuclease III from *E. coli* in mitochondria of breast cancer cells diminishes mitochondrial DNA repair capacity and cell survival after oxidative stress. DNA Repair, 2003. 2(5): p. 471-482.
Shokolenko, I., M. Alexeyev, S. LeDoux, and G. Wilson, TAT-mediated protein transduction and targeted delivery of fusion proteins into mitochondria of breast cancer cells. DNA Repair, 2005. 4(4): p. 511-518.
Shukla, A., M. Jung, M. Stern, N. Fukagawa, D. Taatjes, D. Sawyer, B. Van Houten, and B. Mossman, Asbestos induced mitochondrial DNA damage and dysfunction linked to the development of apoptosis. Am J Physiol Lung Cell Mol Physiol, 2004. 285: p. L1018-L1025.
Simmons, R., I. Suponitsky-Kroyer, and M. Selak, Progressive accumulation of mitochondrial DNA mutations and decline in mitochondrial function lead to beta-cell failure. J Biol Chem, 2005. 280: p. 28785-28791.
Singh, G., S. Sharkey, and R. Moorhead, Mitochondrial DNA damage by anticancer agents. Pharmac ther, 1992. 54: p. 217-230.
Skulachev, V., Why are mitochondria involved in apoptosis? Permiability transition pores and apoptosis as selective mechanisms to eliminate superoxide-producing mitochondria and cells. FEBS Lett, 1996. 397: p. 7-10.
Soga, N., N. Namba, S. McAllister, L. Cornelius, T. SL, S. Dowdy, J. Kawamura, and K. Hruska, Rho family GTPases regulate VEGF-stimulated endothelial cell motility. Exp Cell Res, 2001. 269: p. 73-87.
Victoria Del Gaizo, A Novel TAT-Mitochondrial Sequence Fusion Protein is Processed, Stays in the Mitochondria, and Crosses the Placenta, Molecular Therapy, vol. 7, pp. 720-730, Jun. 2003.
Vocero-Akbani, A., N. Heyden, N. Lissy, L. Ratner, and S. Dowdy, Killing HIV-infected cells by transduction with an HIV protease-activated caspase-3 protein. Nat Med, 1999. 5: p. 29-33.
Wender, P., D. Mitchell, K. Pattabiraman, E. Pelkey, L. Steinman, and J. Rothbard, The design, synthesis, and evaluation of molecules that enable or enhance cellular uptake: peptoid molecular transporters. Proc Natl Acad Sci USA, 2000. 97: p. 13003-13008.
Wilson Glenn L et al: Diabetes, 55(Suppl. 1); A59 (2006), XP008116786.
Wilson, G. and G. KL, Effects of the rodenticide Vacor on cultured rat pancreatic beta cells. Toxicol Appl Pharmacol, 1983. 68: p. 375-379.
Wilson, G., B. D'Andrea, S. Bellomo, and J. Craighead, Encephalomyocarditis virus infection of cultured pancreatic beta cells. Nature, 1980. 285: p. 112-113.
Wilson, G., B. Mossman, and J. Craighead, Use of pancreatic beta cells in culture to identify diabetogenic N-Nitroso compounds. In Vitro, 1983. 19: p. 25-30.
Wilson, G., M. Appel, and W. Chick, Pancreatic islet cell cultures: Immunoperoxidase staining and autoradiography. Tissue Culture Association Manual, 1980. 5: p. 1193-1197.
Wilson, G., N. Patton, and S. LeDoux, Mitochondrial DNA in beta-cells is a sensitive target for damage by nitric oxide. Diabetes, 1997. 46: p. 1291-1295.
Wilson, G., N. Patton, J. McCord, D. Mullins, and B. Mossman, Mechanisms of streptozotocin and alloxan-induced damage in rat beta cells. Diabetologia, 1984. 27: p. 587-591.
Wilson, G., S. Bellomo, and J. Craighead, Effects of interferon on encephalomyocarditis virus infection of cultured mouse pancreatic beta cells. Diabetologia, 1983. 24: p. 38-41.
Yamada et al; Mitochondrion, Elsevier, Amsterdam, NL, 7(1-2); 63-71, (2007),XP005919563.
Zhang, D., J. Mott, P. Farrar, J. Ryerse, S. Chang, M. Stevens, G. Denniger, and H. Zassenhaus, Mitochondrial DNA mutations activate the mitochondrial apoptotic pathway and cause dilated cardiomyopathy. Cardiovascular Res, 2003. 57: p. 147-157.

\* cited by examiner

INS-1E

TAT-GFP    Mito Tracker    Overlay

100 µg 2h

100 µg 12h

Glycerol 12h

Pancreas
Frozen sections

Isolated Islets**

*Intraperitoneal administration followed by islet isolation

1- MTS-GFP-TAT
2- GFP-TAT

Islet Viability: Ethidium Bromide/Acridine Orange[1]

[1] Viable islet cells in green, non-viable islet cells in red
* MTS-Endo3-TAT 1.5 μg/gr body weight i.p. 24 hours before brain death
** Brain Death: 2 hours
Estimated viability: No brain death buffer 87±3%; No brain death MTS-Endo3-TAT 95±2%; brain death buffer 65±4%; brain death MTS-Endo3-TAT 85±5%

SEQUENCE LISTING

```
<160> NUMBER OF SEQ ID NOS: 15

<210> SEQ ID NO 1
<211> LENGTH: 24
<212> TYPE: PRT
<213> ORGANISM: Homo sapiens

<400> SEQUENCE: 1

Met Leu Ser Arg Ala Val Cys Gly Thr Ser Arg Gln Leu Ala Pro Ala
1               5                   10                  15

Leu Gly Tyr Leu Gly Ser Arg Gln
            20
```

-continued

<210> SEQ ID NO 2
<211> LENGTH: 28
<212> TYPE: PRT
<213> ORGANISM: Homo sapiens

<400> SEQUENCE: 2

Met Leu Ser Ala Leu Val Arg Pro Val Ser Ala Leu Arg Arg Ser
1               5                   10                  15

Phe Ser Thr Ser Ala Gln Asn Asn Ala Lys Val Ala
            20                  25

<210> SEQ ID NO 3
<211> LENGTH: 29
<212> TYPE: PRT
<213> ORGANISM: Homo sapiens

<400> SEQUENCE: 3

Met Pro Leu Leu Arg Gly Arg Cys Pro Ala Arg Arg His Tyr Arg Arg
1               5                   10                  15

Leu Ala Leu Leu Gly Leu Gln Pro Ala Pro Arg Phe Ala
            20                  25

<210> SEQ ID NO 4
<211> LENGTH: 32
<212> TYPE: PRT
<213> ORGANISM: Homo sapiens

<400> SEQUENCE: 4

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

<210> SEQ ID NO 5
<211> LENGTH: 42
<212> TYPE: PRT
<213> ORGANISM: Homo sapiens

<400> SEQUENCE: 5

Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe
        35                  40

<210> SEQ ID NO 6
<211> LENGTH: 33
<212> TYPE: PRT
<213> ORGANISM: Homo sapiens

<400> SEQUENCE: 6

Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Ser Val Pro Ala
            20                  25                  30

Ser

<210> SEQ ID NO 7
<211> LENGTH: 35
<212> TYPE: PRT
<213> ORGANISM: Homo sapiens

<400> SEQUENCE: 7

Met Gly Val Phe Cys Leu Gly Pro Trp Gly Leu Gly Arg Lys Leu Arg
1               5                   10                  15

Thr Pro Gly Lys Gly Pro Leu Gln Leu Leu Ser Arg Leu Cys Gly Asp
            20                  25                  30

His Leu Gln
        35

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Gly Arg Lys Lys Arg Arg Gln Arg Arg Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Lys Lys Arg Arg Gln Arg Arg Arg
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 11

His His His His His His His His His His
1               5                   10

<210> SEQ ID NO 12
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgctgagcc gcgcggtgtg cggcaccagc cgccagctgg cgccggcgct gggctatctg    60
ggcagccgcc agggatccat gaataaagca aaacgcctgg agatcctcac tcgcctgcgt   120
gagaacaatc ctcatcccac caccgagctt aatttcagtt cgccttttga attgctgatt   180
gccgtactgc tttccgctca ggcgaccgat gtcagtgtta ataaggcgac ggcgaaactc   240
tacccggtgg cgaatacgcc tgcagcgatg cttgaactgg gcgttgaagg ggtgaaaacc   300
tatatcaaaa cgattgggct ttataacagc aaagcagaaa atatcatcaa aacctgccgt   360
atcttgctgg agcagcataa tggcgaggtt ccggaagatc gtgctgcgct tgaagccctg   420
cccggcgtag tcgtaaaaac agccaacgtc gtattaaaca ctgcattcgg ctggccgact   480
attgctgtcg acacgcacat tttccgcgtt tgtaatcgta ctcaatttgc gccggggaaa   540
aacgtcgaac aggtagaaga aaagctactg aaagtggttc cagcagagtt taaagtcgac   600
tgccaccatt ggttgatcct gcacgggcgt tatacctgca ttgcccgcaa gccccgctgt   660
ggctcttgta ttattgaaga tctttgtgaa tacaaagaga agttgacat cgagctcggc    720
tatccgtatg atgtgccgga ttatgcgagc ctgggctatg ccgcaaaaaa acgccgccag   780
cgccgccgcg ccatcacca tcaccatcac catcaccatc actaa                    825
```

<210> SEQ ID NO 13
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Leu Ser Arg Ala Val Cys Gly Thr Ser Arg Gln Leu Ala Pro Ala
1               5                   10                  15

Leu Gly Tyr Leu Gly Ser Arg Gln Gly Ser Met Asn Lys Ala Lys Arg
            20                  25                  30

Leu Glu Ile Leu Thr Arg Leu Arg Glu Asn Asn Pro His Pro Thr Thr
        35                  40                  45

Glu Leu Asn Phe Ser Ser Pro Phe Glu Leu Leu Ile Ala Val Leu Leu
    50                  55                  60

Ser Ala Gln Ala Thr Asp Val Ser Val Asn Lys Ala Thr Ala Lys Leu
65                  70                  75                  80

Tyr Pro Val Ala Asn Thr Pro Ala Ala Met Leu Glu Leu Gly Val Glu
                85                  90                  95

Gly Val Lys Thr Tyr Ile Lys Thr Ile Gly Leu Tyr Asn Ser Lys Ala
            100                 105                 110

Glu Asn Ile Ile Lys Thr Cys Arg Ile Leu Leu Glu Gln His Asn Gly
        115                 120                 125

Glu Val Pro Glu Asp Arg Ala Ala Leu Glu Ala Leu Pro Gly Val Gly
    130                 135                 140

Arg Lys Thr Ala Asn Val Val Leu Asn Thr Ala Phe Gly Trp Pro Thr
145                 150                 155                 160

Ile Ala Val Asp Thr His Ile Phe Arg Val Cys Asn Arg Thr Gln Phe
                165                 170                 175

Ala Pro Gly Lys Asn Val Glu Gln Glu Glu Lys Leu Leu Lys Val
            180                 185                 190

Val Pro Ala Glu Phe Lys Val Asp Cys His His Trp Leu Ile Leu His
    195                 200                 205

Gly Arg Tyr Thr Cys Ile Ala Arg Lys Pro Arg Cys Gly Ser Cys Ile
```

```
            210                 215                 220
Ile Glu Asp Leu Cys Glu Tyr Lys Glu Lys Val Asp Ile Glu Leu Gly
225                 230                 235                 240

Tyr Pro Tyr Asp Val Pro Asp Tyr Ala Ser Leu Gly Tyr Gly Arg Lys
                245                 250                 255

Lys Arg Arg Gln Arg Arg Gly His His His His His His His
            260                 265                 270

His His
```

<210> SEQ ID NO 14
<211> LENGTH: 1224
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgctgagcc gcgcggtgtg cggcaccagc cgccagctgg cgccggcgct gggctatctg      60
ggcagccgcc agggatcccc ggcccgcgcg ctgctgccgc ccgtatgggc catcgtacc      120
ctggcttcca ccccggcgct gtgggcctca atcccgtgcc cgcgttccga actgcgcctg     180
gatctggttc tgccgagcgg ccagagcttc cgctggcgtg aacagtcccc ggcgcattgg     240
tccggcgtgc tggcggatca ggtttggacg ctgacccaga ccgaagaaca gctgcattgc     300
accgtgtatc gcggcgataa agccaggcg tctcgcccga cgccggatga actggaagcc      360
gttcgtaaat attttcagct ggatgtgacc ctggcgcagc tgtaccacca ctggggctca     420
gtcgattcgc attttcagga agttgcgcag aaatttcagg cgtccgtct gctgcgtcag      480
gacccgatcg aatgtctgtt cagctttatt gcagcagca acaataacat gcgcgcatc      540
acgggtatgg tggaacgtct gtgccaggcg tttggcccgc gcctgattca actggatgat     600
gtcacgtatc acggttttcc gagcctgcag gcgctggcgg tccggaagt ggaagcgcat      660
ctgcgcaaac tgggcctggg ttatcgtgcc cgttatgttt ctgcaagtgc acgcgcgatt     720
ctggaagaac agggcggtct ggcgtggctg cagcaactgc gtgaatcttc atatgaagaa     780
gctcataaag cgctgtgcat cctgccgggt gtgggtacga aagtggcgga ttgtatttgt     840
ctgatggcgc tggataaacc gcaagctgtt ccggttgatg tgcatatgtg gcatatcgcg     900
caacgtgatt atagctggca tccgaccacc agccaggcaa aaggtccgag cccgcagacc     960
aacaaagaac tgggcaactt ctttcgctca ctgtggggtc cgtacgcggg ttgggcacag    1020
gcggtgctgt ttagcgcgga tctgcgtcag tctcgtcatg cgcaggaacc gccggctaaa    1080
cgtcgtaaag gttccaaagg tccggaaggc gatctcggct atccgtatga tgtgccggat    1140
tatgcgagcc tgggctatgg ccgcaaaaaa cgccgccagc gccgccgcgg ccatcaccat    1200
caccatcacc atcaccatca ctaa                                           1224
```

<210> SEQ ID NO 15
<211> LENGTH: 407
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Leu Ser Arg Ala Val Cys Gly Thr Ser Arg Gln Leu Ala Pro Ala
1               5                   10                  15
```

```
Leu Gly Tyr Leu Gly Ser Arg Gln Gly Ser Pro Ala Arg Ala Leu Leu
            20                  25                  30

Pro Arg Arg Met Gly His Arg Thr Leu Ala Ser Thr Pro Ala Leu Trp
        35                  40                  45

Ala Ser Ile Pro Cys Pro Arg Ser Glu Leu Arg Leu Asp Leu Val Leu
 50                  55                  60

Pro Ser Gly Gln Ser Phe Arg Trp Arg Glu Gln Ser Pro Ala His Trp
 65                  70                  75                  80

Ser Gly Val Leu Ala Asp Gln Val Trp Thr Leu Thr Gln Thr Glu Glu
                85                  90                  95

Gln Leu His Cys Thr Val Tyr Arg Gly Asp Lys Ser Gln Ala Ser Arg
            100                 105                 110

Pro Thr Pro Asp Glu Leu Glu Ala Val Arg Lys Tyr Phe Gln Leu Asp
        115                 120                 125

Val Thr Leu Ala Gln Leu Tyr His His Trp Gly Ser Val Asp Ser His
    130                 135                 140

Phe Gln Glu Val Ala Gln Lys Phe Gln Gly Val Arg Leu Leu Arg Gln
145                 150                 155                 160

Asp Pro Ile Glu Cys Leu Phe Ser Phe Ile Cys Ser Ser Asn Asn Asn
                165                 170                 175

Ile Ala Arg Ile Thr Gly Met Val Glu Arg Leu Cys Gln Ala Phe Gly
            180                 185                 190

Pro Arg Leu Ile Gln Leu Asp Asp Val Thr Tyr His Gly Phe Pro Ser
        195                 200                 205

Leu Gln Ala Leu Ala Gly Pro Glu Val Glu Ala His Leu Arg Lys Leu
    210                 215                 220

Gly Leu Gly Tyr Arg Ala Arg Tyr Val Ser Ala Ser Ala Arg Ala Ile
225                 230                 235                 240

Leu Glu Glu Gln Gly Gly Leu Ala Trp Leu Gln Gln Leu Arg Glu Ser
                245                 250                 255

Ser Tyr Glu Glu Ala His Lys Ala Leu Cys Ile Leu Pro Gly Val Gly
            260                 265                 270

Thr Lys Val Ala Asp Cys Ile Cys Leu Met Ala Leu Asp Lys Pro Gln
        275                 280                 285

Ala Val Pro Val Asp Val His Met Trp His Ile Ala Gln Arg Asp Tyr
    290                 295                 300

Ser Trp His Pro Thr Thr Ser Gln Ala Lys Gly Pro Ser Pro Gln Thr
305                 310                 315                 320

Asn Lys Glu Leu Gly Asn Phe Phe Arg Ser Leu Trp Gly Pro Tyr Ala
                325                 330                 335

Gly Trp Ala Gln Ala Val Leu Phe Ser Ala Asp Leu Arg Gln Ser Arg
            340                 345                 350

His Ala Gln Glu Pro Pro Ala Lys Arg Arg Lys Gly Ser Lys Gly Pro
        355                 360                 365

Glu Gly Asp Leu Gly Tyr Pro Tyr Asp Val Pro Asp Tyr Ala Ser Leu
    370                 375                 380

Gly Tyr Gly Arg Lys Lys Arg Arg Gln Arg Arg Gly His His His
385                 390                 395                 400

His His His His His His
            405
```

TREATMENT OF DISEASE CONDITIONS VIA ADMINISTRATION OF DNA REPAIR ENZYME

CROSS-REFERENCE TO RELATED APPLICATIONS

The present application is a continuation of U.S. patent application Ser. No. 12/866,540, filed on Dec. 10, 2010, which application is a national phase entry under 35 U.S.C. §371 of International Application No. PCT/US2009/000889, filed Feb. 9, 2009, which claims priority from U.S. Provisional Patent Application No. 61/065,044 filed Feb. 8, 2008, all of which are incorporated herein by reference.

SEQUENCE LISTING

The instant application contains a Sequence Listing which has been submitted via EFS-Web and is hereby incorporated by reference in its entirety. Said ASCII copy, created on Jul. 29, 2010, is named SAMSF335.txt and is 12,915 bytes in size.

TECHNICAL FIELD

The present invention is directed to compositions and methods for enhancing viability of islets of Langerhans for purposes of transplantation, and for treating various diseases and other abnormal or pathological conditions, with DNA repair enzymes that are directed to the mitochondria.

BACKGROUND ART

Diabetes is a significant health problem worldwide. Present estimates indicate that diabetes is becoming an increasingly prevalent disease which is doubling every 10-15 years, and that by the year 2010 over 250 million people will be afflicted. P. Zimmet, et al., *Diabetes global estimates and projections, ed.* 1994-2010 (1994). Most individuals with idiopathic diabetes can be categorized as having insulin-dependent diabetes mellitus (type I diabetes) or noninsulin-dependent diabetes mellitus (type II diabetes). Although the etiologies and clinical manifestations of these two syndromes differ, it has become increasingly clear that a critical lesion in many of the subgroups under these large classifications is at the level of the β-cell. Mandrup-Poulsen, Biochem Pharmacol 66:1433-40 (2003); Halban, et al., Diabetologia 47:581-89 (2004).

Although new treatment protocols have had a significant impact on life expectancy and quality of life of individuals with either form of diabetes, there still remains no cure. Insulin treatment for absolute or relative insulin-deficiency cannot adequately compensate for the loss of physiological insulin secretion. Intra-hepatic islet transplantation is a promising strategy in connection with type I diabetes. Unfortunately, this approach has been plagued by the loss of function and viability of islet cells during isolation and in the early transplantation period. Weir, et al., Arch. Med. Res. 36:273-80 (2005). This has caused a dramatic increase in the number of islets required for transplantation, which has significantly impacted the amount of islets available for transplant. Additionally, this problem has contributed greatly to the graft failure that has been seen in most transplant recipients over time. See, Gaglia, et al., Arch. Med. Res. 36:273-80 (2005); Weir, et al., supra. Therefore, there is a belief that functional loss and death of β-cells play a predominant role in the pathogenesis of both types of diabetes and in the failure of islet transplants.

Inflammatory bowel disease (IBD), more common forms of which include Crohn's disease and ulcerative colitis, affects a staggering number of people in developed countries, estimated at around 0.1% of the population. As a group, these disorders are characterized by unrelenting inflammation of the lower gastrointestinal tract leading to periodic and sometimes chronic bouts of diarrhea, profound abdominal distress, malnutrition, and other symptoms. Pathologically, the colonic mucosa of afflicted individuals is overtly disrupted and shows signs if intense inflammation with invasion of commensal organism from the intestinal lumen into the mucosal wall. The cause of IBD remains unknown, although it is believed that both genetics and environmental factors make a significant contribution.

Ischemic heart disease (IHD) continues to be a leading cause of death and of health care expense in the United States. Although there are myriad risk factors for IHD (e.g., smoking, hypertension and obesity). In diabetic and obese prediabetic patients, there is a growing consensus about the growth of coronary collaterals being impaired. See, Abaci, et al., Circulation 99:2239-42 (1999); Kornowski, Coron. Artery Dis. 14:61-4 (2003); Turhan, et al., Coron. Artery Dis. 16:281-85 (2005); Waltenberger, Cardiovasc. Res. 49:554-60 (2001). This is critical because the presence of well-developed coronary collateral circulation makes an important impact on the morbidity and mortality associated with coronary disease. See, Hansen, Am. Heart J. 117:290-95 (1989). Because 30-40% of patients demonstrate an absence of a coronary collateral circulation and are at much higher risk of developing complications in the event of a coronary occlusion, new therapies are essential to protect these individuals.

Acute lung injury and the acute respiratory distress syndrome (ALI/ARDS) are syndromes of acute onset arising with non-cardiogenic pulmonary edema development, manifest as bilateral infiltrates on the chest radiograph coupled to acute hypoxic respiratory failure. Currently, it is estimated that 16%-18% of all ICU patients develop ALI/ARDS producing 6,368,000 hospital days per year in health care costs. The mortality estimates of patients suffering from this syndrome are still 30-50%. Recent estimates of incidence in the United States are around 190,000 cases of ALI and ARDS per year. These numbers are actually projected to rise with the aging of the population and the projected increase in severe sepsis cases, which is the most common cause of ALI/ARDS. See, Ware, et al., N. Eng. J. Med. 353:2788-96 (2005).

Bronchopulmonary dysplasia (BPD) is one such example of an acute lung disease that occurs primarily in preterm infants who require supplemental oxygen. Although the advent of surfactant therapy and use of high frequency low tidal volume ventilator approaches have improved the survival rates of extremely low birth weight infants, significant morbidity and mortality continues to be associated with BPD. In a recent review of clinical data, BPD was shown to be the most costly disease per child and second only to asthma in overall costs. See, Ireys, et al., Pediatrics 100:197-204 (1997). Due to the high rate of premature births and the recent increase in multiple births, BPD is rapidly becoming a common and costly healthcare challenge.

It was estimated that in 2005, approximately 18,500 new cases of primary central nervous system (CNS) tumors would be diagnosed and 12,760 deaths from primary CNS tumors would occur in the United States. See, Jemal, et al., Can. Cancer. J. Clin. 53:5-26 (2003). The majority of these deaths result from malignant gliomas. The optimum therapeutic modality presently consists of surgical tumor resection followed by radiotherapy and chemotherapy. The relationship between increased survival and increased radiotherapy dose was demonstrated by Walker, et al, Int. J. Radiat. Oncol. Biol. Phys. 5:1725-31 (1979). However, the total dose of radiation that can be administered safely is limited by the risk of normal brain morbidity. This can lead to devastating functional deficits several months to years after irradiation. See, Sheline, et al., Int. J. Radiat. Oncol. Biol. Phys. 6:1215-28 (1980); Leibel, et al., Int. J. Radiat. Oncol. Biol. Phys. 17:1129-39 (1989). Thus, in practice, the radiation dose applied to the brain must be limited. The need to both understand and minimize the side effects of brain irradiation is enhanced by the ever-increasing number of patients with secondary brain metastases that require treatment with large field or whole brain irradiation (WBI). Approximately 200,000-250,000 patients will be diagnosed with brain metastases in 2005, making this the second most common site of metastatic cancer as well as the most common neurological manifestation of cancer. Brain metastases are more common in incidence than newly diagnosed lung, breast, or prostate cancer. Currently, approximately 175,000 cancer patients per year receive large field or WBI. Yet, at the present time, there are no successful treatments for radiation-induced brain injury, nor are there any known effective preventive strategies.

SUMMARY OF THE INVENTION

A first aspect of the present invention is directed to method of enhancing viability of islets of Langerhans (β-cells) for purposes of transplantation, comprising contacting the β-cells with a composition comprising a multi-domain conjugate or fusion protein comprising a protein transduction domain, a mitochondrial targeting sequence and a DNA repair enzyme, in an amount effective to enhance viability of the β-cells.

In some embodiments, the contacting is achieved by administering the fusion protein to a recipient of a β-cell transplant, such as a type-I or type-II diabetic. In other embodiments, the contacting is achieved by administering the fusion protein to a donor of β-cells. In yet other embodiments, the contacting is achieved by storing the β-cells in a medium containing the fusion protein after they have been harvested from the donor. In yet other embodiments, the contacting is achieved by administering the fusion protein to both the donor and the recipient, optionally in combination with storage of the β-cells in fusion protein-containing medium. In some embodiments, the protein transduction domain contains a TAT protein or is related to a TAT protein, the mitochondrial targeting sequence comprises or is derived from an MNSOD sequence, and/or the DNA repair enzyme comprises or is related to human 8-oxoguanine DNA glycosylase (hOGG1).

A second aspect of the present invention is directed to a composition comprising a culture of β-cells and a composition comprising a multi-domain conjugate comprising a protein transduction domain, a mitochondrial targeting sequence and a DNA repair enzyme, in an amount effective to enhance viability of the β-cells. A related aspect is directed to the multi-domain conjugate, per se (e.g., which may be prepared recombinantly in the form of a continuous protein or fusion protein). Thus, this aspect is directed to a chimeric peptide, polypeptide or protein comprising a protein transduction domain, a mitochondrial targeting sequence and a DNA repair enzyme, linked together directly or indirectly (e.g., via a linking group) via covalent or peptide bonds.

A third aspect of the present invention is directed to a method of treating inflammatory bowel disease, comprising administering to a patient in need thereof, a composition comprising a multi-domain conjugate or fusion protein comprising a protein transduction domain, a mitochondrial targeting sequence and a DNA repair enzyme, in a therapeutically effective amount.

A fourth aspect of the present invention is directed to a method of treating ischemic heart disease, comprising administering to a patient in need thereof, a composition comprising a multi-domain conjugate or fusion protein comprising a protein transduction domain, a mitochondrial targeting sequence and a DNA repair enzyme, in a therapeutically effective amount.

A fifth aspect of the present invention is directed to a method of treating acute lung injury or acute respiratory distress syndrome, comprising administering to a patient in need thereof, a composition comprising a multi-domain conjugate or fusion protein comprising a protein transduction domain, a mitochondrial targeting sequence and a DNA repair enzyme, in a therapeutically effective amount. In one embodiment, the acute lung injury is bronchopulmonary dysplasia.

A sixth aspect of the present invention is directed to a method of treating radiation induced-brain injury, comprising administering to a patient in need thereof, a composition comprising a multi-domain conjugate or fusion protein comprising a protein transduction domain, a mitochondrial targeting sequence and a DNA repair enzyme, in a therapeutically effective amount.

Without intending to be bound by theory, Applicants hypothesize that an acceptable lesion equilibrium is normally maintained in mitochondrial DNA (mtDNA) in all cells through a balance between the damage to mtDNA caused by the normal endogenous production of reactive oxygen species (ROS) as a byproduct of oxidative phosphorylation and its subsequent repair. However, this equilibrium is altered during the pathogenesis of type I diabetes, the isolation of islets for transplantation, ischemic bowel and heart disease, acute lung injury, and radiation therapy due to increased exposure to elevated levels of ROS and reactive nitrogen species (RNS), resulting in increased damage to mtDNA. This causes alterations in mtDNA transcription to ensue, either through base mispairing which results in defective transcripts, or decreased transcription due to RNA polymerase blocking. Either process will change key electron transport complexes to cause decreased ATP production and alter the reduction of $O_2$ to $H_2O$, so that more one electron reductions of $O_2$ will occur. This will cause enhanced amounts of reactive oxygen species (ROS) to be produced. This increased production of ROS and decreased ATP generation will exacerbate the ongoing stress in the cells and lead to defective normal cellular functions. As this process continues, mitochondrial genomes will become increasingly mutated, further decreasing the pool of viable genomes and intensifying the oxidative stress in the cell. When this process reaches a critical level, the cell will die, either through apoptotic, necrotic, or mixed necroapoptotic processes. The present invention aborts this vicious cycle in its initial stages, and normalizes or at least inhibits further damage to mtDNA, thus enhancing cell viability.

DETAILED DESCRIPTION OF THE INVENTION

Figure 1:
FIG. 1 shows co-localization of MTS-GFP-TAT fluorescent signal with MitoTracker dye, wherein INS-1E cells were incubated with 80 μg/ml pf MTS-GFP-TAT in culture medium for 12 h, and wherein prior to fixation, cells were incubated with MitoTracker Red CN—$H_2$OROS. The left panel shows the green fluorescence of the GFP, thus indicating the presence of the fusion protein; the middle panel shows the red fluorescence of MitoTracker for the same cells, thereby revealing the location of the mitochondria; and the right panel shows overlapping of the green and red signals to give a yellow color indicative of co-localization of the fusion protein and the MitoTracker in mitochondria.
Figure 1:
Figure 1:
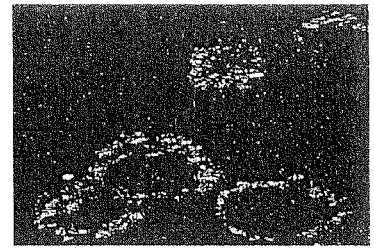

The Fusion Proteins
Mitochondrial Targeting Sequence

As used herein, the term Mitochondrial targeting Sequence (MTS) refers to a signal containing a polypeptide that directs a molecule to a specific organelle namely a mitochondrion.

The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure.

Mitochondrial localization/targeting sequences generally consist of a leader sequence containing positively charged amino acids. This allows the protein to be targeted to the highly negatively charged mitochondria. Unlike receptor:ligand approaches that rely upon stochastic Brownian motion for the ligand to approach the receptor, the mitochondrial localization signal is drawn to mitochondria because of charge. Thus, in some embodiments, the mitochondrial localization sequence contains at least two, and in some embodiments about 5-15, or about 11 charged groups.

In order to enter the mitochondria, a protein generally must interact with the mitochondrial import machinery, consisting of the Tim and Tom complexes (Translocase of the Inner/Outer Mitochondrial Membrane). With regard to the mitochondrial localization sequence, the positive charge draws the fusion protein to the complexes and continues to draw the fusion protein into the mitochondria. The Tim and Tom complexes allow the proteins to cross the membranes.

Representative examples of mitochondrial localization sequences that may be useful in the present invention include human manganese superoxide dismutase (hMnSOD, aa 1-24) MLSRAVCGTSRQLAPALGYLGSRQ (SEQ ID NO:1) (from Genbank CAA42066); mitochondrial isoform of human malate dehydrogenase (MDH2, aa 1-28) MLSALVRPVSAALRRSFSTSAQNNAKVA (SEQ ID NO.:2) (from Genbank CAG38785); human cytochrome c oxidase subunit VIII (COX, aa 1-29) MPLLRGRCPARRHYRRLALLGLQ-PAPRFA (SEQ ID NO.:3) (from Genbank Q7Z4L0); human ornithine transcarbamoylase (OTC, aa 1-32) MLFNL-RILLNNAAFRNGHNFMVRNFRCGQPLQ (SEQ ID NO.: 4) (from Genbank AAI07154); human mitochondrial transcription factor A (TFAM, aa 1-42) MAFLRSMWGVLSALGRSGAELCTGCGSR-LRSPFSFVYLPRWF (SEQ ID NO.:5) (from Genbank NP_003192) human DNA polymerase γ (PolG, aa 1-33) MSRLLWRKVAGATVGPGPVPAPGRWVSSSVPAS (SEQ ID NO.:6) (from Genbank NP_002684); and human uracil DNA glycosylase (UNG1, aa 1-35) MGVFCLGP-WGLGRKLRTPGKGPLQLLSRLCGDHLQ (SEQ ID NO.: 7) (from Genbank CAA61579). Yet other examples that may be useful in the present invention are set forth in Table 1 in U.S. Patent Application Publication 20070196334.

DNA Repair Protein or Enzyme

Cells have evolved the capacity to remove or tolerate lesions in their DNA. The most direct mechanisms for repairing DNA are those that simply reverse damage and restore DNA to its normal structure in a single step. A more complex mechanism, excision repair, involves incision of the DNA at the lesion site, removal of the damaged or inappropriate base(s), and resynthesis of DNA using the undamaged complementary strand as a template. This system of repair can further be categorized into base and nucleotide excision repair. These enzymes can be used in the practice of the present invention.

Base excision repair involves two major classes of repair enzymes, namely, N-glycosylases and AP endonucleases DNA N-glycosylases are enzymes that hydrolyze the N-glycosidic bond between the damaged base and the deoxyribose moiety, leaving behind an AP site on the DNA backbone. AP sites produced by the action of N-glycosylases are acted upon by AP endonucleases, which can make an incision either 3' to the AP site (class I AP lyase) or 5' to the AP site (class II AP endonuclease). All those enzymes shown to contain class I AP lyase activity possess an associated DNA glycosylase activity; however, not all glycosylases are AP lyases. Class II AP endonucleases are the major enzymes responsible for the repair of AP sites in DNA.

Several DNA glycosylases have been identified. They are classified into two major families: 1) enzymes that possess only DNA glycosylase activity; and 2) enzymes that contain both a DNA glycosylase activity and an associated class I AP lyase activity; that is, enzymes that catalyze a β-elimination cleavage of the phosphodiester bond 3' to an AP site.

The major cellular enzymes initiating the repair process for AP sites, the so-called "class II" AP endonucleases, have been identified and characterized in bacteria, yeast and mammalian systems, including human cells. These repair proteins hydrolyze the phosphodiester backbone immediately 5' to an AP site generating a normal 3'-hydroxyl nucleotide which can prime DNA repair synthesis. Moreover, these enzymes have also been shown to contain repair activity for 3'-terminal oxidative lesions. By hydrolyzing 3'-blocking fragments from oxidized DNA, these enzymes can produce normal 3'-hydroxyl nucleotide termini, permitting DNA repair synthesis.

In *E. coli*, the major AP endonuclease enzymes are exonuclease III and endonuclease IV. Exonuclease III comprises approximately 90% of the cellular AP endonuclease activity and greater than 95% of the total activity for removal of blocked 3' ends. Endonuclease IV accounts for much of the residual activity.

Exonuclease III is the major class II AP endonuclease in *E. coli* and incises on the 5' side of an AP site, leaving a 3' hydroxyl and a 5' phosphate. This 3' hydroxyl group is a substrate for DNA polymerases. In addition to its AP endonuclease activity, exonuclease III demonstrates phosphodiesterase, exonuclease, phosphatase and RNAse H activities.

Endonuclease IV, encoded by the nfo gene, is the other main class II AP endonuclease of *E. coli*. Like exonuclease III, endonuclease IV exhibits many activities such as phosphatase, phosphodiesterase, as well as endonuclease activity against DNA containing urea residues.

*S. cerevisiae* contains a single major AP endonuclease/3'-repair diesterase encoded by the APN1 gene. Apn1 protein has been reported to have many biochemical properties in common with endonuclease IV.

AP endonucleases have been purified to apparent homogeneity from a variety of mammalian sources including mouse, *drosophila*, calf thymus, human placenta, and HeLa cells (Seki, et al., J. Biol. Chem. 266:20797-20802 (1991); Haukanes, et al., Nucleic Acids Res. 17(4):1493-1509 (1989); Ivanov, et al., Eur. J. Biochem. 172(1):155-9 (1988); Henner, et al., Nucleic Acids Res. 5(14):5529-44 (1987); Cesar, et al., J. Biochem. 129(3):509-517 (1983); Shaper, et al., J. Biol. Chem. 257(22):13455-8 (1982); and Kane, et al., J. Biol. Chem. 256(7):3405-14 (1981)). The activities have similar molecular weights around 37 kDa and require magnesium. Each of these enzymes appears to be a class II AP endonuclease.

Sequences of specific DNA repair enzymes proteins that may be useful in the present invention include those from the base excision repair (BER) pathway, e.g., AP endonucleases such as human APE (hAPE, Genbank Accession No. M80261) and related bacterial or yeast proteins such as APN-1 (e.g., Genbank Accession No. U33625 and M33667), exonuclease III (ExoIII, xth gene, Genbank Accession No. M22592,) bacterial endonuclease III (EndoIII, nth gene, Genbank Accession No. J02857), huEndoIII (Genbank Accession No. U79718), and endonuclease IV (EndoIV nfo gene Genbank Accession No. M22591). Additional BER proteins suitable for use in the invention include, for example, DNA glycosylases/AP lyases such as, formamidopyrimidine-DNA glycosylase (FPG, Genbank Accession No. X06036), endonuclease VIII like 1 (NEIL1 *Homo sapiens* Genbank Accession No. AAH10876} endonuclease VIII-Like (NEIL2 *Homo sapiens* Genbank Accession No. AAH13964), Glycosylases such as human 3-alkyladenine DNA glycosylase (HAAG, also known as human methylpurine-DNA glycosylase (hMPG, Genbank Accession No. M74905), NTG-1 (Genbank Accession No. P31378 or 171860), SCR-1 (YAL015C), SCR-2 (Genbank Accession No. YOL043C), DNA ligase I (Genbank Accession No. M36067), β-polymerase (Genbank Accession No. M13140 (human)) and 8-oxoguanine DNA glycosylase (OGG1 Genbank Accession No. U44855 (yeast); Y13479 (mouse); Y11731 (human)). Proteins for use in the invention from the direct reversal pathway include human MGMT (Genbank Accession No. M29971) and other similar proteins.

Protein Transduction Domain

A Protein Transduction Domain or PTD refers to a polypeptide compounds that facilitates traversing a lipid bilayer, micelle, or cell membrane. The PTD allows the fusion protein, or at least the DNA repair enzyme and the mitochondrial targeting sequence to traverse the islet cell membranes, for example and move from extracellular space to intracellular space, or cytosol. Suitable PTDs for use in the present invention include the TAT PTD YGRKKRRQRRR (SEQ ID NO:8), the basic domain Tat(49-57) which is RKKRRQRRR (SEQ ID NO.:9); 11 arginine residues, and positively charged polypeptides or polynucleotides having 8-15 residues, preferably 9-11 residues. Several modifications to TAT, including substitutions of glutamine to alanine, have been reported to demonstrate an increase in cellular uptake anywhere from 90% to up to 33 fold in mammalian cells. Other suitable PTDs include penetratin, which is the PTD of the *Drosophila* homeotic transcription factor Antennapedia. Penetratin is an active domain of this protein and consists of the 16-amino acid sequence RQIKIWFQNR-RMKWKK (SEQ ID NO.:10).

The fusion proteins of the present invention may be prepared in accordance with standard techniques. In some embodiments, for example, the fusion proteins are expressed in *E. coli* and purified from bacterial lysate using metal affinity chromatography. The general procedure for the expression and purification of the proteins is as follows. Competent *E. coli* cells are transformed with plasmid DNA containing the protein of interest using an electroporation procedure. Transformed bacteria are grown in liquid culture media under optimized conditions to produce a sufficient bacterial mass. Bacterial pellets are harvested by centrifugation and bacterial cells are subsequently lysed by a sonication procedure. Clarified bacterial lysates contain the protein of interest in soluble form. Ni-NTA agarose is subsequently added to the lysates to specifically bind the recombinant histidine tag—containing the protein of interest. After washing off and the unbound material, the bound protein is eluted from Ni-NTA agarose with buffer containing a high concentration of imidazole. When necessary, gel-filtration chromatography is then used to remove the imidazole and/or exchange the salt composition in the eluted protein buffer.

DNAs encoding mitochondrial localization sequences, DNA repair proteins or enzymes and protein transduction domains are known in the art. To prepare a chimeric DNA molecule containing fragments encoding each of these domains, for purposes of expression in a host to produce a fusion protein wherein each domain is linked via a peptide bond, the respective DNA fragments may be individually assembled (e.g., using recursive PCR) and then ligated together in accordance with standard techniques. The chimeric DNA may further contain sequences e.g., to facilitate detection of other recombinant proteins (e.g., a HA tag) through the use of specific antibodies to the tag, or to facilitate purification of the expression product (e.g., a polyhistidine tag containing about 10 His residues (SEQ ID NO.:11)). The chimeric DNA molecules are preferably constructed so that the DNA repair protein is sandwiched between the mitochondrial targeting sequence and the protein transduction domain in order to protect the mitochondrial targeting sequence from cleavage. Exemplary chimeric DNA molecules encoding fusion proteins of the present invention, and the corresponding amino acid sequences are set forth below.

```
pIS1 MTS (hMnSOD 1-24)-EndoIII-TAT
                                              (SEQ ID NO.: 12)
atgctgagccgcgcggtgtgcggcaccagccgccagctggcgccggcgctgggctatctgggcagccg
ccagggatccatgaataaagcaaaacgcctggagatcctcactcgcctgcgtgagaacaatcctcatc
ccaccaccgagcttaatttcagttcgccttttgaattgctgattgccgtactgctttccgctcaggcg
accgatgtcagtgttaataaggcgacggcgaaactctacccggtggcgaatacgcctgcagcgatgct
tgaactgggcgttgaaggggtgaaaacctatatcaaaacgattgggctttataacagcaaagcagaaa
atatcatcaaaacctgccgtatcttgctggagcagcataatggcgaggttccggaagatcgtgctgcg
cttgaagccctgcccggcgtaggtcgtaaaacagccaacgtcgtattaaacactgcattcggctggcc
gactattgctgtcgacacgcacattttccgcgtttgtaatcgtactcaatttgcgccggggaaaaacg
tcgaacaggtagaagaaaagctactgaaagtggttccagcagagtttaaagtcgactgccaccattgg
ttgatcctgcacgggcgttatacctgcattgcccgcaagcccgctgtggctcttgtattattgaaga
tctttgtgaatacaaagagaaagttgacatcgagctcggctatccgtatgatgtgccggattatgcga
gcctgggctatggccgcaaaaaacgccgccagcgccgccgcggccatcaccatcaccatcaccatcac
catcactaa Amino acid sequence (MTS-EndoIII-TAT) pIS1
                                              (SEQ ID NO.: 13)
mlsravcgtsrqlapalgylgsrqgsmnkakrleiltrlrennphpttelnfsspfelliavllsaqa
tdvsvnkataklypvantpaamlelgvegyktyiktiglynskaeniiktcrilleqhngevpedraa
```

-continued

```
lealpgvgrktanvvlntafgwptiavdthifrvcnrtqfapgknveqveekllkvvpaefkvdchhw
lilhgrytciarkprcgsciiedlceykekvdielgypydvpdyaslgygrkkrrqrrrghhhhhhhh
hh* pIS2 MTS-OGG1-TAT
                                                      (SEQ ID NO.: 14)
atgctgagccgcgcggtgtgcggcaccagccgccagctggcgccggcgctgggctatctgggcagccg
ccagggatccccggcccgcgcgctgctgccgcgccgtatgggccatcgtaccctggcttccaccccgg
cgctgtgggcctcaatcccgtgcccgcgttccgaactgcgcctggatctggttctgccgagcggccag
agcttccgctggcgtgaacagtccccgcgcattggtccggcgtgctggcggatcaggtttggacgct
gacccagaccgaagaacagctgcattgcaccgtgtatcgcggcgataaaagccaggcgtctcgcccga
cgccggatgaactggaagccgttcgtaaatattttcagctggatgtgacccggcgcagctgtaccac
cactggggctcagtcgattcgcattttcaggaagttgcgcagaaatttcagggcgtccgtctgctgcg
tcaggacccgatcgaatgtctgttcagctttatttgcagcagcaacaataacattgcgcgcatcacgg
gtatggtggaacgtctgtgccaggcgtttggcccgcgcctgattcaactggatgatgtcacgtatcac
ggttttccgagcctgcaggcgctggcgggtccggaagtggaagcgcatctgcgcaaactgggcctggg
ttatcgtgcccgttatgtttctgcaagtgcacgcgcgattctggaagaacagggcggtctggcgtggc
tgcagcaactgcgtgaatcttcatatgaagaagctcataaagcgctgtgcatcctgccgggtgtgggt
acgaaagtggcggattgtatttgtctgatggcgctggataaaccgcaagctgttccggttgatgtgca
tatgtggcatatcgcgcaacgtgattatagctggcatccgaccaccagccaggcaaaaggtccgagcc
cgcagaccaacaaagaactgggcaacttctttcgctcactgtggggtccgtacgcgggtgggcacag
gcggtgctgtttagcgcggatctgcgtcagtctcgtcatgcgcagaaccgccggctaaacgtcgtaa
aggttccaaaggtccggaaggcgatctcggctatccgtatgatgtgccggattatgcgagcctgggct
atggccgcaaaaaacgccgccagcgccgcgcggccatcaccatcaccatcaccatcactaa Amino acid sequence (MTS-OGG1-TAT) pIS2
                                                      (SEQ ID NO.: 15)
Mlsravcgtsrqlapalgylgsrqgsparallprrmghrtlastpalwasipcprselrldlvlpsgq
sfrwreqspahwsgvladqvwtltqteeqlhctvyrgdksqasrptpdeleavrkyfqldvtlaqlyh
hwgsvdshfqevaqkfqgvrllrqdpieclfsficssnnniaritgmverlcqafgprliqlddvtyh
gfpslqalagpeveahlrklglgyraryvsasarailleeqgglawlqqlressyeeahkalcilpgvg
tkvadciclmaldkpqavpvdvhmwhiaqrdyswhpttsqakgpspqtnkelgnffrslwgpyagwaq
avlfsadlrqsrhaqeppakrrkgskgpegdlgypydvpdyaslgygrkkrrqrrrghhhhhhhhhh
```

The chimeric DNAs are typically introduced into hosts (cells or organisms) via a vector, which is generally regarded as a carrier nucleic acid molecule into which a nucleic acid sequence can be inserted for introduction into at least one cell where it can be replicated. The chimeric DNAs may be situated in the vector so as to be in operable association with one or more regulatory or other genetic elements, including promoters and enhancers that effectively directs the expression of the DNA in the host chosen for expression, initiation signals and internal ribosome binding sites, multiple cloning sites, splicing sites, termination signals, polyadenylation signals, origins of replication, and selectable markers.

A variety of vectors may be useful in connection with the present invention, depending upon the host. In the case of bacterial hosts, plasmids are appropriate. Vectors containing the chimeric DNAs of the present invention may be delivered to hosts using known techniques, including direct delivery of DNA such as by injection, electroporation, calcium phosphate precipitation, DEAE-dextran followed by polyethylene glycol, direct sonic loading, liposome mediated transfection, receptor-mediated transfection, microprojectile bombardment, agitation with silicon carbide fibers, *Agrobacterium*-mediated transformation, PEG-mediated transformation of protoplasts and desiccation/inhibition-mediated DNA uptake. The targets may be stably or transiently transformed.

Representative hosts include prokaryotes and eucaryotes alike, including bacteria, yeast, animal cells and plant cells.

Following introduction of the chimeric DNAs into the host, the host is cultured under conditions suitable for expression of the chimeric DNA. The expression production is then extracted or harvested from the host, followed by purification. All such procedures, which vary from host to host, are known in the art.

Constructing TAT-PTD fusion proteins and producing them in relatively large amounts can be advantageously practiced in bacterial expression vectors. See, Schwarse, et al., Science 285:1569-72 (1998). In this system, in-frame polyhistidine-TAT fusion proteins are purified from a bacterial lysate under denaturing conditions through a series of affinity, ion exchange, and desalt columns.

In other embodiments, the fusion proteins are constructed non-recombinantly, in which case the polypeptide domains (e.g., the MLS, DNA repair enzyme/protein and the PTD) are linked together via covalent bonds, e.g., disulfide bonds. See, Wagstaff and Jans, Curr. Med. Chem. 13, 1371, 2006.

The fusion proteins of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Methods of Using the Fusion Proteins

The terms "effective amount" and "effective to treat," as used herein, refer to an amount or concentration of the fusion proteins of the present invention utilized for period of time (including acute or chronic administration and periodic or continuous administration) that is effective within the context of its administration for causing an intended effect or physiological outcome.

Enhancing Viability of Islets of Langerhans

For example, in the context of enhancing viability of islets of Langerhans, the term "effective amount" includes amounts that achieve the enhancement of the viability of islets. Effective amounts of the fusion proteins for use in the present invention include, for example, amounts that are effective for enhancing survival and/or improving function of islet cells in vivo and/or in vitro. Within the context of transplantation of individual islet cells or masses of islet cells, e.g., transplant donors and/or recipients, an effective amount of the fusion protein is that amount administered to the transplant donor and/or recipient sufficient to enhance survival of the cell or mass of cells, e.g. to reduce loss of the cell, or mass of cells, and/or to improve functional performance of a transplanted cell or a mass of cells. Within the context of treating cells outside a body, e.g., islet cells to be cultured and/or used for transplantation, an effective amount of the fusion protein is that amount with which the cells are incubated or stored in order to enhance preservation of the cells and/or to reduce cell loss, e.g., loss via apoptosis, and/or to enhance function. As used herein, the term "inhibiting" includes delaying the onset of, reducing, preventing, or alleviating a biological process, e.g., apoptosis.

The term "patient" is used throughout the specification to describe an animal, human or non-human, to whom treatment according to the methods of the present invention is provided. Veterinary applications are clearly anticipated by the present invention. The term "donor" or "donor patient" as used herein refers to an animal (human or non-human) from whom islet cells can be obtained for the purposes of storage and/or transplantation to a recipient patient. The term "recipient" or "recipient patient" refers to an animal (human or non-human) into which islet cells can be transferred.

The term "diabetes" is a general term to describe diabetic disorders as they are recognized in the art, e.g., Diabetes Mellitus. Diabetes Mellitus is characterized by an inability to regulate blood glucose levels. The two most prevalent types of diabetes are known as Type I and Type II diabetes. In Type I, or insulin-dependent diabetes (IDDM), the pancreas makes little or no insulin because the insulin-producing β-cells have been destroyed. In Type II, or noninsulin-dependent diabetes (NIDDM), the pancreas makes some insulin but the insulin is not effective. The term also encompasses the myriad secondary disorders caused by diabetes, both acute and chronic, e.g., diabetic complications, e.g., hypoglycemia and hyperglycemia, retinopathy, angiopathy, neuropathy, nephropathy, insulin-resistance, syndrome X, and the involvement of advanced glycation end products (AGE) in neuropathy and atherosclerosis.

The term "islet cell(s)" is used throughout the specification as a general term to describe the clumps of cells within the pancreas known as islets, e.g., islets of Langerhans. Islets of Langerhans contain several cell types that include, e.g., β-cells (which make insulin), α-cells (which produce glucagons), γ-cells (which make somatostatin), F cells (which produce pancreatic polypeptide), enterochromaffin cells (which produce serotonin), PP cells and D1 cells.

By "isolated cell" is meant that the cell is removed from the tissue or organ in which it (or its predecessor) naturally occurs. A cell can be just partially purified from its natural milieu and be deemed "isolated." For example, an intact islet of Langerhans is considered to be made up of "isolated" cells, once the islet is removed from a pancreas and can be physically separated from other islets.

The term "transplantation" is used throughout the specification as a general term to describe the process of implanting mass of islet cells, or individual islet cells into a patient. The term "transplantation" is defined in the art as the transfer of living tissues or cells from a donor to a recipient, with the intention of maintaining the functional integrity of the transplanted tissue or cells in the recipient (see, e.g., The Merck Manual, Berkow, Fletcher, and Beers, Eds., Merck Research Laboratories, Rahway, N.J., 1992). The term "cell transplantation" is used throughout the specification as a general term to describe the process of transferring at least one islet cell to a patient. For example, such transplantation can be performed by removing the β-cells (or intact islets) from a donor's pancreas and putting them into a recipient patient whose pancreas cannot produce sufficient insulin. The terms include all categories of transplants known in the art, except blood transfusions. Transplants are categorized by site and genetic relationship between donor and recipient. The term includes, e.g., autotransplantation (removal and transfer of cells or tissue from one location on a patient to the same or another location on the same patient), allotransplantation (transplantation between members of the same species), and xenotransplantation (transplantations between members of different species).

The terms "transplant rejection" or "rejection" are art-recognized, and are used throughout the specification as general terms to describe the process of rejection of cells in a recipient. Included within the definition are, for example, three main patterns of rejection that are usually identified in clinical practice: hyperacute rejection, acute rejection, and chronic rejection (see, e.g., Oxford Textbook of Surgery, Morris and Malt, Eds., Oxford University Press, 1994).

The present invention contemplates the use of fusion protein compositions to treat donors, recipients, masses of islet cells, and/or individual islet cells at any step of the harvesting, storage and transplant process. A mass of cells or individual islet cells may be harvested from a donor, treated with a fusion protein composition ex vivo in accordance with the present invention, and transplanted into a recipient. Alternatively or in addition, islet cells can be treated in situ, while still in the donor. Optionally, a fusion protein composition can be administered to the recipient prior to, during, and/or after the surgery with the recipient's blood. The fusion protein may also be administered to the donor prior to or during the process of harvesting the islet cells.

Islet cells can be harvested from a donor and transplanted by any methods known to those of skill in the art (see, for example, Oxford Textbook of Surgery, Morris and Malt, Eds., Oxford University Press (1994)). The skilled practitioner will recognize that methods for harvesting and transplantation may vary depending upon many circumstances, such as the type of donor.

It is further contemplated by the present invention that the methods described herein can be used with islet cells ex vivo, such as a bioartificial pancreas (see, e.g., Sambanis et al., Cytotechnology 15:351-363 (1994)). The cells (or masses of cells) can be treated with the fusion protein either prior to putting them in the device, or while they are utilized in the device, or both. Alternatively or in addition, the donor animal can be administered fusion protein prior to removal of the islet cells for use in the device.

Alternatively or in addition, a cell can be cultured as described below and transplanted into a recipient.

In the context of the other diseases and conditions disclosed herein, inflammatory bowel disease includes for example, patients with Crohn's disease and ulcerative colitis. Other, less common forms of IBD include indeterminate colitis, infectious colitis (viral, bacterial or protozoan, e.g., amoebic colitis), pseudomembranous colitis (necrotizing colitis), and ischemic inflammatory bowel disease.

Crohn's disease is characterized by intestinal inflammation and the development of intestinal stenosis and fistulas. Neuropathy often accompanies these symptoms. Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus. Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis is also known to cause problems such as arthritis, inflammation of the eye, liver disease (hepatitis, cirrhosis, and primary sclerosing cholangitis), osteoporosis, skin rashes, and anemia. A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum.

Without intending to be bound by any particular theory of operation, Applicants hypothesize that the fusion proteins of the present invention suppresses IBD symptoms by ameliorating or even preventing persistent inflammatory injury (mediated by fragmentation of mitochondrial DNA) to the mucosal barrier.

Ischemic heart disease (IHD) includes coronary arteriosclerosis, angina pectoris, and acute and old myocardial infarction and refers to the serious disorder of the vital heart that mostly affects males and females in late middle age or older. Coronary arteriosclerosis is characterized by arteriosclerosis in the coronary artery that supplies nutrients to the heart. Angina pectoris is characterized by attacks of chest pain caused by impaired blood flow in the coronary artery. Myocardial infarction is characterized by myocardial necrosis caused by impaired blood flow in the coronary artery and by fatal complications coming there with such as arrhythmia, cardiac failure, cardiac rupture, and pump failure. Impaired blood flow to the heart, a vital organ, is an essential characteristic of these ischemic heart diseases. IHD patients who may be particularly suitable for treatment in accordance with the methods of the present invention include diabetics (e.g., type II diabetics) and obese pre-diabetics. Ischemic heart disease can be diagnosed using well-known techniques. See, e.g., U.S. Patent Application Publication 20080146498 A1. According to U.S. Patent Application Publication 20080081997 A1, conclusive diagnosis of ischemic heart disease is given by coronary angiography.

Without intending to be bound by any particular theory of operation, Applicants hypothesize that the fusion proteins of the present invention may exert a beneficial effect on coronary collateral growth, activation (e.g., phosphorylation) of key kinases in diabetics, maintain mitochondrial integrity, maintain mitochondrial energy production, and combinations thereof.

As used herein, "acute lung injury" refers to a critical illness syndrome consisting of acute hypoxemic respiratory failure with bilateral pulmonary infiltrates that are not attributed to left atrial hypertension. See, e.g., Rubenfeld, et al., N. Engl. J. Med. 353:1685-93 (2005). Acute lung injury also refers to a syndrome of life-threatening progressive pulmonary insufficiency or hypoxemic respiratory failure in the absence of known pulmonary disease (such as emphysema, bronchitis, or chronic obstructive pulmonary disease), usually following a systemic insult such as surgery or major trauma. In embodiments of the methods of the present invention, the acute lung injury is induced by diseases or disorders other than pulmonary diseases. In some embodiments of the methods of the present invention, the acute lung injury is pulmonary injury caused/induced by an extrapulmonary origin such as neurogenic pulmonary injury, secondary to severe CNS (central nervous system) trauma. In some embodiments of the methods of the present invention, the acute lung injury is acute lung injury induced by extrapulmonary diseases. In some embodiments of the methods of the present invention, the acute lung injury is indirect pulmonary injury from trauma, sepsis, and other disorders such as acute pancreatitis, drug overdose. In some embodiments of the methods of the present invention, the acute lung injury is acute lung injury induced by inhalation of noxious fumes, burn, or massive blood transfusion. In some embodiments of the methods of the present invention, the acute lung injury is acute lung injury induced by peritonitis during sepsis, acute lung injury induced by intravenous bacteremia during sepsis, acute lung injury caused by smoke inhalation, acute lung injury occurring in a premature infant with deficiency of surfactant, acute lung injury caused by oxygen toxicity or acute lung injury caused by barotrauma from mechanical ventilation. Thus, symptoms of acute lung injury may include lung hemorrhage, hyaline membrane formation, lung lesion, lung edema, lung inflammation, increased transvascular fluid flux, prevalent interstitial edema and alveolar collapse, and combinations thereof.

BPD affects 20-60% of all premature, very low birth weight infants. BPD is associated with substantial morbidity and mortality as well as extremely high health care costs. Although the widespread use of intra-tracheally administered exogenous surfactant and antenatal steroid therapy has reduced the overall severity of BPD, the prevalence of this condition has actually increased, due in part to improved survival of very low birth weight infants. More specifically, BPD is associated with alveolar simplification, capillary malformations, and interstitial cellularity. See, e.g., Coalson, Semin. Neonatol. 8:73-81 (2003). This impaired alveolar formation leads to a long-term reduction in alveolar number and a decrease in the gas-exchange surface area. While a variety of risk factors predispose infants to BPD, it has been reported that supplemental oxygen remains one of the prime sufficient conditions for its development. See, e.g., Chess, et al., Semin. Perinatol. 30:171-78 (2006). Thus, BPD is a multi-factorial disease process that is the end result of an immature, surfactant-deficient lung that has been exposed to hyperoxia, mechanical ventilation and infection.

To treat (and even prevent) BPD, the fusion proteins of the present invention may be administered during the first few days of life of a premature infant, thus providing improved lung function. The fusion proteins may be administered with or without, and before or after surfactant therapy. Thus, treatment with the fusion proteins may be initiated during the first day of an infant patient's life, e.g., within about 30 minutes of intubation and receipt of surfactant. Premature infants are typically intubated for the purposes of administering oxygen and inflating their lungs, which would collapse without intubation. Thus, premature or preterm infant patients are also suitable for treatment in accordance with the inventive methods. Intubation can then serve as a direct route for the intratracheal administration (also known as endotracheal administration) of medicines, such as surfactants, to the lungs. Thus the fusion proteins may be administered intra-tracheally as well as parenterally (e.g., injection into the muscle tissues or intravenous injection). Since problems related to BPD can persist, the present invention also contemplates administration not only to infants, but to adolescents and even adults if necessary.

ARDS is also known in the medical literature as stiff lung, shock lung, pump lung and congestive atelectasis, and its incidence has been estimated to be 1 out of 100,000 people. ARDS is accumulation within the lung which, in turn, causes the lung to stiffen. The condition is triggered by a variety of processes that injure the lungs. In general, ARDS occurs as a medical emergency. It may be caused by a variety of conditions that directly or indirectly cause the blood vessels to "leak" fluid into the lungs. In ARDS, the ability of the lungs to expand is severely decreased and damage to the alveoli and lining (endothelium) of the lung is extensive. The concentration of oxygen in the blood remains very low in spite of high concentrations of supplemental oxygen which are generally administered to a patient. Among the systemic causes of lung injury are trauma, head injury, shock, sepsis, multiple blood transfusions and medications. Pulmonary causes include pulmonary embolism, severe pneumonia, smoke inhalation, radiation, high altitude, near drowning, and more.

ARDS symptoms usually develop within 24 to 48 hours of the occurrence of an injury or illness. It is believed that cigarette smoking may be a risk factor. Among the most common symptoms of ARDS are laboured, rapid breathing, nasal flaring, cyanosis blue skin, lips and nails caused by lack of oxygen to the tissues, breathing difficulty, anxiety, stress and tension. Additional symptoms that may be associated with this disease are joint stiffness and pain and temporarily absent breathing. The diagnosis of ARDS is commonly done by testing for symptomatic signs. A simple chest auscultation or examination with a stethoscope, for example, will reveal abnormal breath sounds which are symptomatic of the condition. Confirmatory tests used in the diagnosis of ARDS include chest X-rays and the measurement of arterial blood gas. In some cases ARDS appears to be associated with other, diseases, such as patients with acute myelogenous leukemia, who developed acute tumour lysis syndrome (AILS) after treatment with cytosine arabinoside. In general, however, ARDS appears to be associated with traumatic injury, severe blood infections such as sepsis, or other systemic illness, the administration of high dose radiation therapy and chemotherapy, and inflammatory responses which lead to multiple organ failure, and in many cases death.

Based on the time of clinical expression, radiation-induced brain injury has been described in terms of acute, early delayed and late delayed reactions Tofilon, et al., Radiat. Res. 153:357-70 (2000). Acute injury, expressed days to weeks after irradiation, is fairly rare under current radiotherapy regimens. Early delayed injury occurs from 1-6 months post-irradiation and can involve transient demyelination with somnolence. While both of these early injuries can result in severe reactions, they are normally reversible and resolve spontaneously. In marked contrast, late delayed effects, characterized by demyelination, vascular abnormalities and ultimate white matter necrosis (Schultheiss, et al., Br. J. Radiol. 65:737-53 (1992)), are observed for more than 6 months post-irradiation and are viewed as irreversible and progressive. In addition to these histopathologic endpoints, there is a growing awareness of intellectual deterioration in patients receiving brain irradiation. Crossen, et al., J. Clin. Oncol. 12:627-42 (1994). Thus, patients falling into any of these categories may be treated in accordance with the methods of the present invention. The fusion proteins can be administered before irradiation, or after irradiation.

Cognitive dysfunction, including dementia, induced by large field or WBI is reported to occur in 20-50% of brain tumor patients who are long-term survivors (greater than 15 months post-irradiation). Crossen, et al., supra; Imperato, et al., Ann. Neurol. 28:818-22 (1990); and Johannesen, et al., Radiother. Oncol. 69:169-76 (2003). Thus, these patients may be treated in accordance with the methods of the present invention.

For purposes of practicing any of the methods of the present invention, the fusion protein compositions can be combined in admixture with a pharmaceutically acceptable carrier or vehicle, optionally with other excipients (e.g., wetting agents, dispersing agents, surfactants, stabilizers, preservatives, etc.). The term "pharmaceutically acceptable carrier" refers to a carrier or adjuvant that may be administered to a patient, together with a fusion protein of this invention, and which does not destroy the pharmacological activity of the fusion protein and is nontoxic when administered in doses sufficient to deliver a therapeutic amount of the fusion protein. Therapeutic compositions are prepared by mixing the fusion protein with the carrier. They are typically formulated as reconstitutable lyophilized formulations or aqueous or oily solutions, dispersions, suspensions, or emulsions. Accordingly, acceptable carriers and other excipients include water, saline, fixed oils such as mono- and diglycerides, buffers such as phosphate, citrate and other organic acids (e.g., HEPES based buffer containing KCl, BSA and glycerol, pH 7.5); antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG ion exchangers, alumina, aluminum stearate, lecithin, and self-emulsifying therapeutic agent delivery systems (SEDDS) such as D-α-tocopherol polyethyleneglycol 1000 succinate.

The compositions of the present invention can be administered to patients in need thereof (e.g., an in the case of islet preservation, both donors and recipients), in accordance with well-known techniques and sound medical practice. One such mode is parenteral administration. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. The compositions described herein are typically administered by injection, e.g., intravenously, intra-arterially, subdermally, intraperitoneally, intramuscularly, subcutaneously or intraductually. Intravenous administration is advantageous in terms of rapid delivery of the fusion protein throughout the body. In the case of islet preservation, intraductal administration to the common bile duct affords direct delivery of the fusion protein to the pancreas of donors or into the liver of recipients which is a site of transplantation. Intraperitoneal administration is relatively easy, but requires relatively more fusion protein. Other than modes described herein, further modes of administration e.g., intranasal and via suppository, might also be useful.

Thus, parenteral formulations containing the fusion protein may be prepared, packaged, or sold in a form suitable for bolus administration or for continuous administration. The formulations may be prepared, packaged, or sold in unit dosage form, such as in ampules or in multi-dose containers.

In terms of administration to human for any of the indications disclosed herein, dosage amounts of the fusion proteins generally ranges from about 1 to about 100 mg/kg of patient body weight. Some variation in the actual dosage amount will necessarily occur depending on physical and physiological factors such as the body weight and overall condition of the subject being treated including the type and severity of the disease or condition, as well as the route of administration and the molecular weight of a given fusion protein. The person responsible for administration will, in any event, determine the appropriate dose for the individual subject. Experiments conducted with rats (and which are described in the working examples below) showed positive results with dosages of an embodiment of the present invention, as it pertains to the preservation of islets, ranging from 1.5 to 2.5 µg/g of body weight. Animal experiments provide reliable guidance for the determination of effective doses for human therapy, so interspecies scaling of effective doses can be performed following the principles laid down by Mordenti, J. and Chappell, W. "The use of interspecies scaling in toxicokinetics," in *Toxicokinetics and New Drug Development*, Yacobi et al., Eds., Pergamon Press, New York 1989, pp. 42-96. Lower or higher doses than those recited above may be required.

The timing and duration of treatment of the diseases and conditions disclosed herein are also variable, taking into account various factors including the half-life of the fusion proteins, which is approximately 72 hours. For example, in embodiments of the present invention pertaining to islet preservation, the fusion protein is administered to the donor prior to harvesting the islets, and to the recipient at the time of transplantation and at about 48-hour intervals thereafter as needed. Success of treatment (and the need for continuation of treatment) can be determined by assessing the number of islet equivalents required to maintain euglycemia in the recipient. Enhancement of the viability of the islets can also be evaluated via glucose tolerance tests and radioimmunoassay for insulin and/or C-peptide.

Cell Culture

In some embodiments of the present invention, the islets can be treated with the fusion proteins in vitro. The method can include the steps of providing a vessel containing the fusion protein, providing the islet cell in vitro and then culturing or simply maintaining in the presence of the fusion protein. In vitro treatment is advantageously performed immediately following harvesting of the islets from the donor and for the duration of storage prior to transplantation.

The method can be performed in any vessel suitable for culturing or holding islet cells, such as roller bottles, cell culture flasks, petri dishes, and test tubes.

The skilled practitioner will appreciate that culture conditions, e.g., temperature, can be selected and/or varied (see, for example, Cells: A Laboratory Manual, Spector and Leinwand, Eds., Cold Spring Harbor Laboratory Press, Cold Spring Harbor, N.Y., 1997). For example, the murine insulinoma cell line βTC3 (DSMZ, Braunschweig, Germany) can be incubated in humidified 5% $CO_2$/95% air at 37° C.

The islet cell may be disposed, e.g., suspended or bathed in, a liquid medium. The medium can be any medium known to those of skill in the art to be suitable for culturing, preserving, or washing the islet cells of interest (see, for example, Cells: A Laboratory Manual, Spector and Leinwand, Eds., Cold Spring Harbor Laboratory Press, Cold Spring Harbor, N.Y., 1997). Such types of media include, but are not limited to, various buffers, Eagle's minimal essential medium (MEM), Dulbecco/Vogt modified Eagle's minimal essential medium (DMEM), or Roswell Park Memorial Institute (RPMI) Medium. Such media may also comprise appropriate supplements, e.g., fetal bovine serum (FBS), individual amino acids, antibiotics, and/or vitamins. For example, the medium can be RPMI medium 1640 (Life Technologies, Grand Island, N.Y.) supplemented with 2 mM L-glutamine, 100 U/ml penicillin G, 100 U/ml streptomycin and 10% Fetal Calf Serum (FCS) (Life Technologies). The concentration of the fusion protein in the medium will generally range from about 1 µg/ml to about 100 µg/ml, and in some embodiments, about 25 µg/ml to 100 µg/ml.

In the context of transplantation, the present invention further contemplates that other procedures known in the art for enhancing graft survival/function can be used along with the methods described herein. Such procedures include, but are not limited to immunosuppressive therapies and donor specific transfusions (DSTs). For example, a DST can be administered to a recipient prior to, during and/or after the administration of CO, HO-1, other heme-associated products, and/or NO to a recipient. Such administration, e.g., administration of DST(s) along with a treatment described herein, can be carried out prior to, during, and/or after transplantation.

Embodiments of the present invention are now described in connection with the following non-limiting examples.

EXAMPLE 1

To show that the TAT protein can effectively target proteins to mitochondria in beta cells, the β cell line INS-1E was exposed to the fusion protein MTS-TAT-GFP. The experimental protocol was as follows: INS-1E cells were grown in RPMI 1640 medium containing 10 mmol/l HEPES, 10% fetal bovine serum, 50 µmol/l 2-mercaptoethanol, 50 µg/ml gentimicine sulfate, and 1 µmol/l pyruvate. The solution of MTS-GFP-TAT in the elution buffer was added directly to the medium in the culture dish to a final concentration of 80 µg/ml. After 12 h of incubation with the fusion protein, cells were trypsinized and replated onto glass cover slips. After attachment, cells were fixed in 4% formaldehyde, washed with PBS and mounted on a glass slide using a SlowFade Antifade Kit. To visualize mitochondria, live cells were incubated prior to fixation with 1 µM of Mito-Tracker Red CM-$H_2$ XRos for 15 mins. Cells were observed by florescent microscopy. As shown in FIG. 1, the TAT was efficiently taken up into the INS-1E cells and co-localized with Mitotraker.

Figure 2:
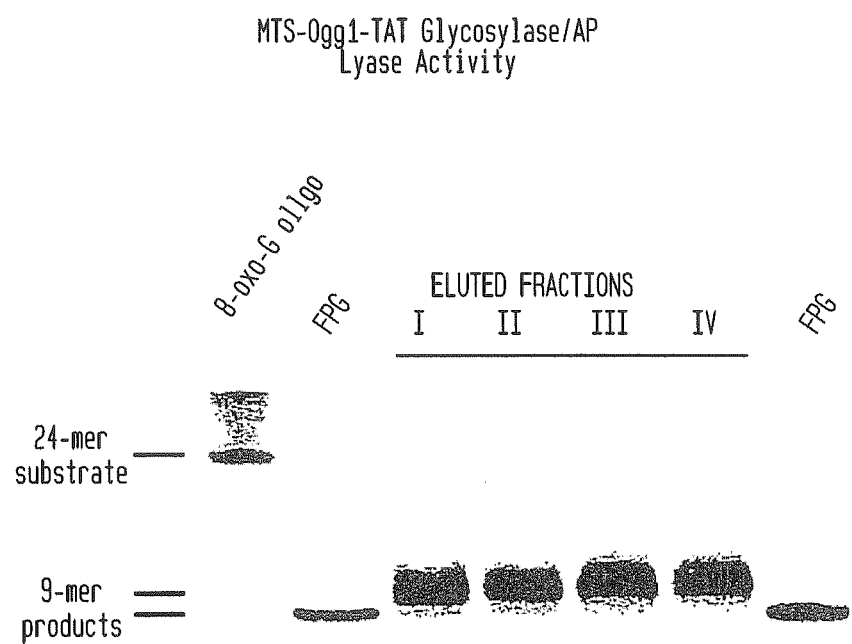
FIG. 2 is an electrophoretic gel stain showing MTS-OGG1-TAT glycosylase/AP lyase activity, using Fapyglycosylase (FPG) as a control. All four of the elution fractions off the Ni column had robust enzymatic activity as only product is seen. The product is slightly lower because this enzyme works through β, δ, elimination, while OGG1 cleaves by only β.
Figure 3:
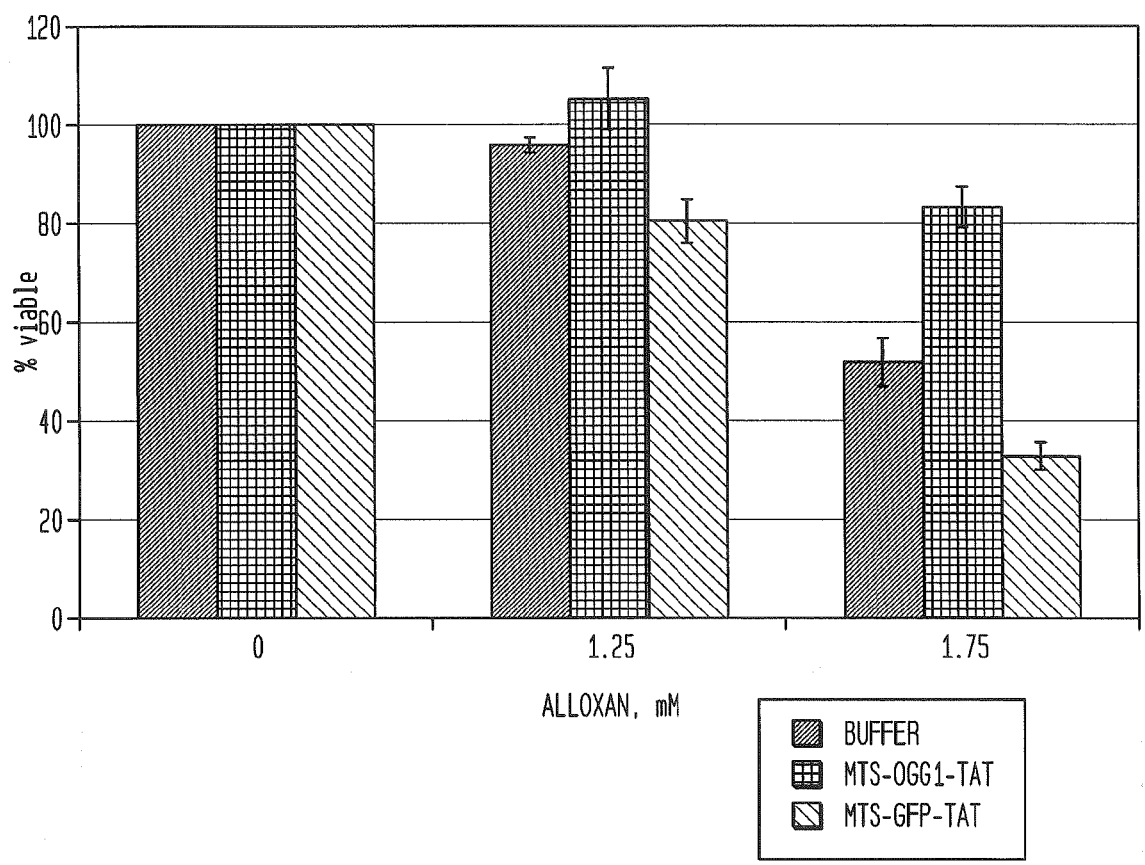
FIG. 3 is a bar graph showing viability of INS-1 cells treated with 80 μg MTS-OGG1-TAT for 2 hours, followed by exposure to either 1.25 or 1.5 mM of the diabetogen alloxan. An MTT assay for cell viability was performed 24 hours later. The results illustrated in this figure show that the fusion protein protected against the toxic effects of alloxan at both concentrations tested.

We next replaced GFP in the construct with OGG1. Enzyme activity assays of the protein off the column showed that all four elution fractions had enzyme activity (FIG. 2). Therefore, we treated INS-1 cells with 80 µg/ml of the MTS-OGG1-TAT 2 hrs before treatment with alloxan and found significant protection 24 hrs later as determined by the MTT assay (FIG. 3). Interestingly, the MTS-GFP-TAT actually exacerbated the alloxan toxicity, indicating that the protection was not due to the presence of the fusion protein, but was the result of the enzyme activity.

Figure 4:
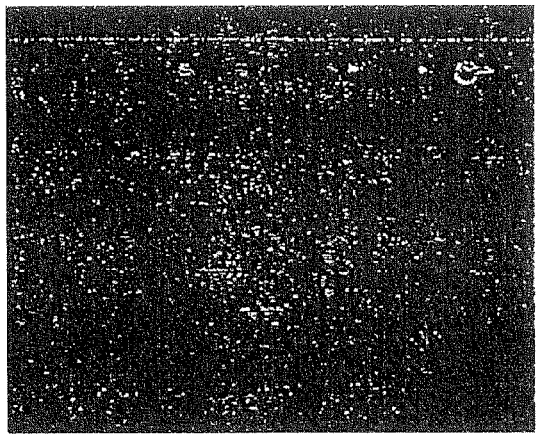
FIG. 4 contains photos of frozen mouse pancreas sections after the mice were injected with either 100 μg of MTS-GFP-TAT or glycerol buffer (as a control). The progressive increase in green fluorescence over time in the pancreata from mice receiving the fusion protein shows that the protein was taken up by the pancreas in these animals.
Figure 4:
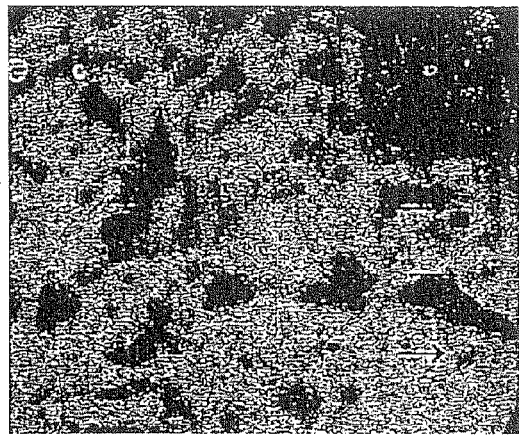
Figure 4:
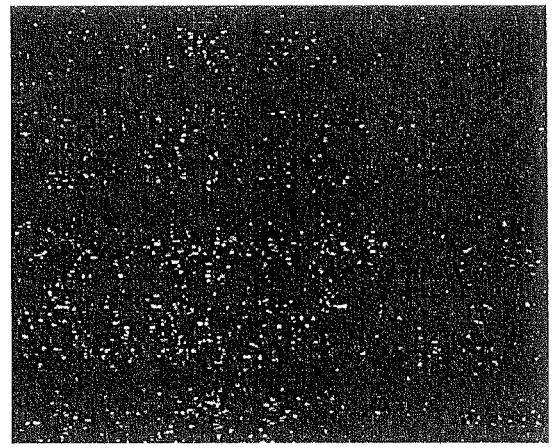

Finally, to explore whether the fusion proteins would work in vivo, we obtained IACUC approval to do a pilot study using mice. Two mice were injected i.v. with 100 µg of MTS-GFP-TAT diluted in glycerol buffer (phosphate buffered saline containing 0.25% glycerol). Another mouse received glycerol buffer only. One of the MTS-GFP-TAT mice was euthanized after 2 hr and its pancreas removed and frozen in liquid nitrogen for frozen sections. At 12 hr post injection, the other mouse receiving MTS-GFP-TAT and the control mouse were euthanized and their pancreata removed and frozen in liquid nitrogen for frozen sections. Pictures were made using identical exposure and contrast settings. See FIG. 4. Despite challenges with the tissue remaining flat on the slide, which obscured somewhat the morphology of the pancreas, it is readily apparent that all of the endocrine and exocrine cells in the pancreas took up the florescent protein in a time-dependent fashion (note the dramatic increase in the uptake of fluorescent protein between 2 and 12 hr) and that its location in the cell is perinuclear (see arrows; round, dark spots are nuclei), which according to our in vitro studies is indicative of uptake into mitochondria. These data provide a high degree of confidence for successful delivery of the fusion proteins of the present invention to mitochondria in virtually all the islet cells in the pancreas.

EXAMPLE 2

In vivo Experiments

Figure 5:
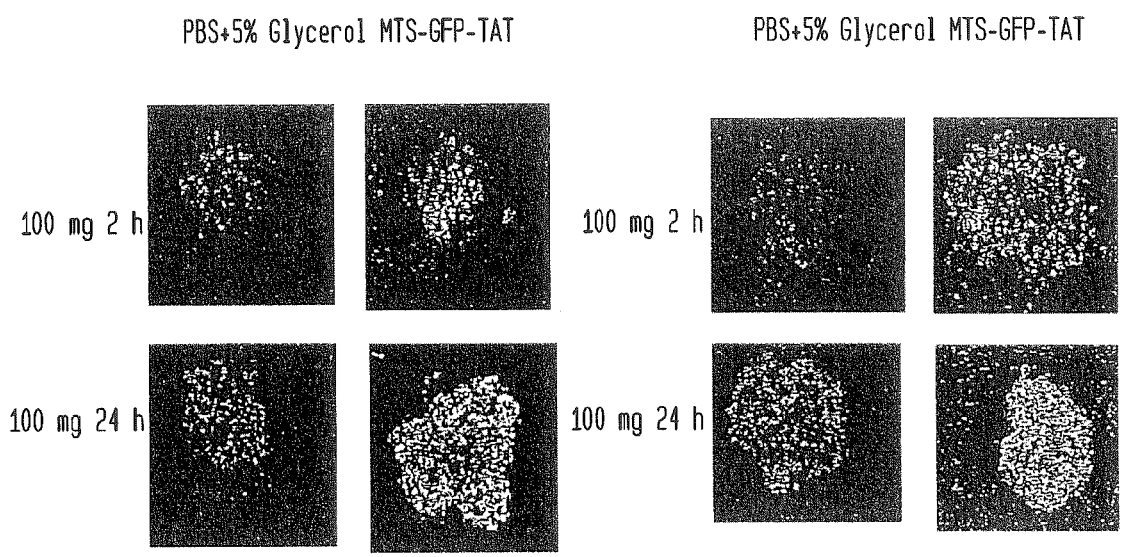
FIG. 5 contains photos of islets isolated from rats after injection with MTS-GFP-TAT or glycerol buffer. The rats were injected intraperitoneally (ip) with recombinant protein containing the TAT sequence, the mitochondrial targeting sequence from MnSOD and GFP. At 2 or 24 hours, the rats were euthanized, pancreata removed and islets isolated. The results illustrated in this figure make it clear that following i.p. injection, the fusion protein accumulated in islets over time and was found throughout the islets after 24 hrs. Islets from rats 2 hrs after injection are only faintly green indicating that the cells are only beginning to take up the protein.
Figure 6:
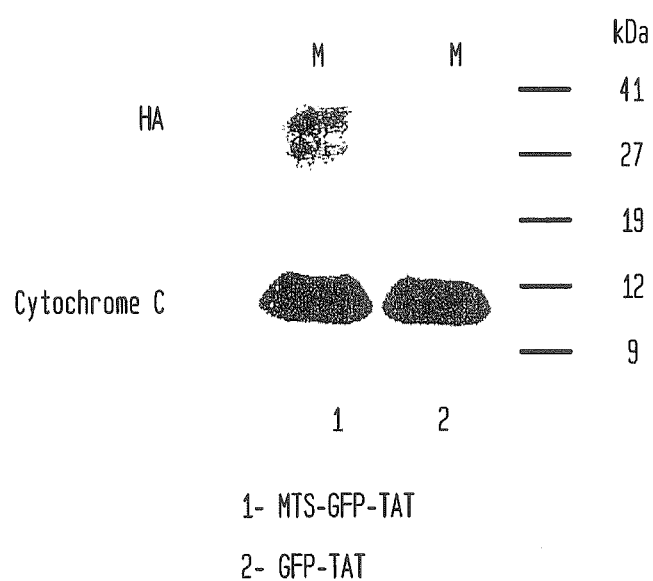
FIG. 6 contains photos of Western blots performed to detect the presence of MTS-GFP-TAT and absence of GFP-TAT in the rat islet mitochondrial protein. Rats were injected i.p. with 1 μg/g body weight with either fusion protein containing a mitochondrial targeting sequence (MTS-GFP-TAT) or fusion protein without the MTS (GFP-TAT). After 24 hrs, the animals were euthanized and islets isolated. The islets from each group (MTS-GFP-TAT or GFP-TAT) were pooled to obtain sufficient tissue for analysis. The mitochondria were isolated by differential centrifugation. Western blots were performed on the protein extracted from the mitochondrial preps. Because the fusion proteins contained an HA tag, the blots were probed with antibody for HA to reveal the presence of the fusion protein in mitochondria. Membranes also were probed with antibodies to cytochrome C to ensure even loading of the mitochondrial proteins. Only islets from animals who received the MTS-GFP-TAT had a band which corresponded to the fusion protein.

To determine whether TAT proteins could be delivered to islets, a pilot study was conducted in which Lewis rats were injected intraperitoneally (i.p.) with recombinant protein containing the TAT sequence, the mitochondrial localization sequence from MnSOD and GFP. At 2 or 24 hours, the rats were euthanized, pancreata removed and islets isolated. It is clear from this study (FIG. 5), that following i.p. injection of the fusion protein it accumulated in islets over time and was found throughout the islets after 24 hrs. A subsequent study was conducted using Western blot analysis to determine whether the fusion protein was targeted to mitochondria. Three rats were injected i.p. with 1 μg/g body weight of either fusion protein containing a mitochondrial targeting sequence (MTS-GFP-TAT), or fusion protein without the MTS (GFP-TAT). After 24 hrs the animals were euthanized and islets were isolated. The islets from each group (MTS-GFP-TAT or GFP-TAT) were pooled to obtain sufficient tissue for analysis and mitochondria isolated by differential centrifugation. Western blots were performed on the protein extracted from the mitochondrial preps. Because the fusion proteins contained an HA tag the blots were probed with antibody for HA to reveal the presence of the fusion protein in mitochondria. Membranes also were probed with antibodies to Cytochrome C to ensure even loading of the mitochondrial proteins. Only islets from animals who received the MTS-GFP-TAT had a band which corresponded to the fusion protein (FIG. 6).

Figure 7:
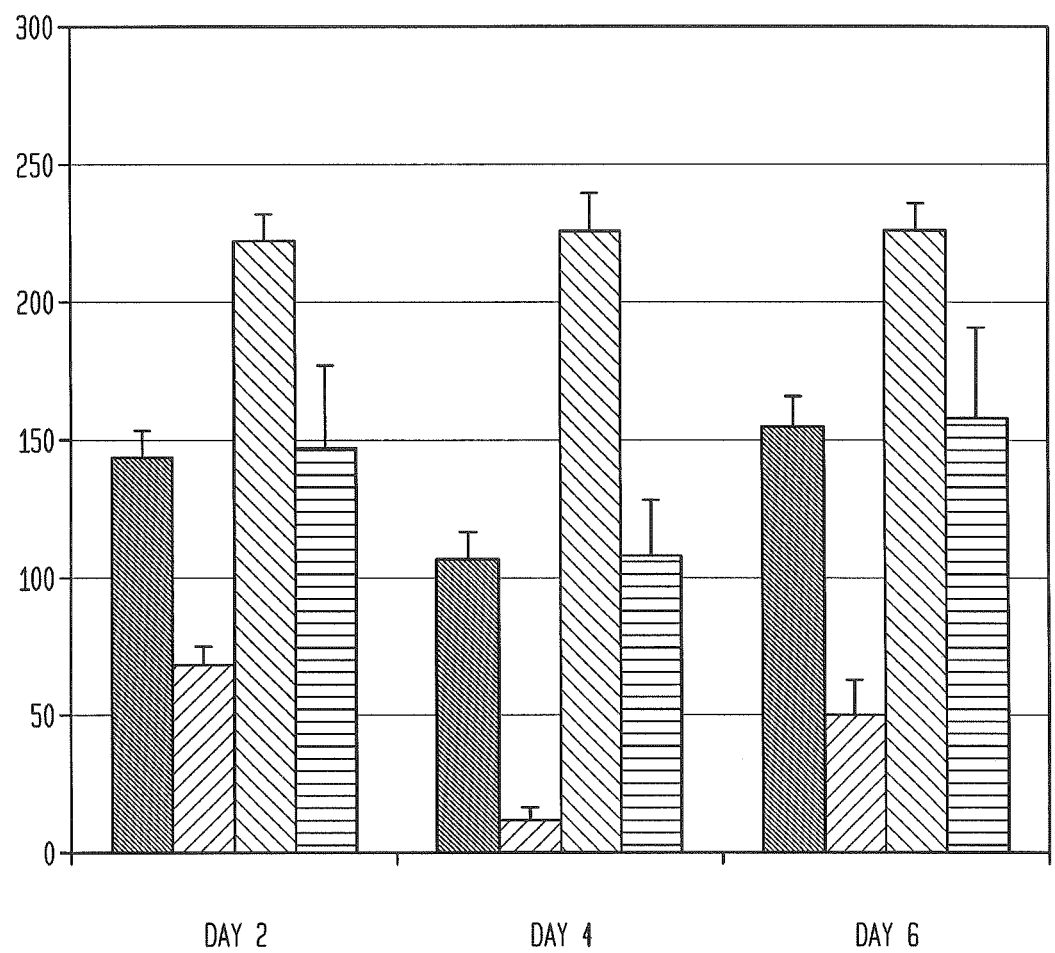
FIG. 7 is a bar graph showing data produced from an experiment designed to assess the ability of a fusion protein of the present invention to protect insulin secretion in beta cells undergoing oxidative stress. Cultures of normal beta cells obtained from neonatal rats were given normal culture medium containing 300 mg/dl glucose. After 48 hrs the medium was removed and saved for radioimmunoassay of insulin (IRI). Two groups of cultures (4 cultures in each group) were replenished with culture medium containing the fusion protein MTS-OGG1-TAT (80 μg/ml). Two groups of controls were given only elution buffer (EB). The next day cultures were treated with 1 mM alloxan in HBSS or HBSS alone for 20 mins. The cultures were replenished with medium containing 300 mg/dl glucose. After 48 hrs the medium was removed, saved for IRI, and the cultures replenished with the same high glucose-containing medium. This process was repeated two more times. The saved culture medium was assayed for insulin and the results expressed as a percentage of the insulin released by the culture before the experimental treatment, which corrected for the differences in cell number in different cultures which occur when β-cells are cultured in monolayer. As shown in this figure, insulin secretion fell precipitously in cultures treated with alloxan and EB due to massive cell death. However, in cultures receiving the fusion protein plus alloxan, insulin secretion was held at control levels because cell death was blocked. Moreover, in cultures treated with the fusion protein only, as in the case of the INS-1 cells, cell function was actually enhanced. Without intending to be bound by any particular theory of operation, Applicant believes that this result is due to the fact that cultured β-cells are under heightened stress due to the high glucose concentration and the hyperoxia occurring in these culture conditions. The fusion protein protected these cells from this stress.

Studies were then performed using normal β-cells in monolayer culture. After establishment of cultures and removal of fibroblasts using published procedures [Nelson, et al., Diabetes 42:1187-94 (1993); LeDoux, et al., Diabetes 35:866-72 (1986); Wilson, et al., Diabetologia 27:587-91 (1984); Wilson, et al., Diabetes 46:1291-95 (1997); Wilson, et al., In Vitro 19:25-30 (1983); Wilson, Toxicol. Appl. Pharmacol. 68:375-9 (1983); Wilson, et al., Nature 285:112-3 (1980); Wilson, et al., Diabetologia 24:38-41 (1983); and Wilson, et al., *Pancreatic islet cell cultures: Immunoperoxidase staining and autoradiography*. Tissue Culture Association Manual, 1980. 5:p. 1193-97], cultures were given normal culture medium containing 300 mg/dl glucose. After 48 hrs the medium was removed and saved for radioimmunoassay of insulin (IRI). Two groups of cultures (4 cultures in each group) were replenished with culture medium containing MTS-OGG1-TAT (80 μg/ml) and two groups of controls were given only elution buffer (EB). The next day cultures were treated with 1 mM alloxan in HBSS or HBSS alone for 20 mins. The cultures were replenished with medium containing 300 mg/dl glucose. After 48 hrs the medium was removed, saved for IRI, and the cultures replenished with the same high glucose-containing medium. This process was repeated two more times. The saved culture medium was assayed for insulin and the results expressed as a percentage of the insulin released by the culture before the experimental treatment, which allowed correction for the differences in cell number in different cultures which occur when β-cells are cultured in monolayer. The results of these (FIG. 7) show that insulin secretion fell precipitously in cultures treated with alloxan and EB due to massive cell death. However, in cultures receiving the fusion protein plus alloxan, insulin secretion was held at control levels because cell death was blocked. Moreover, in cultures treated with the fusion protein only, as in the case of INS-1 cells, cell function was actually enhanced. Again, and without intending to be bound by any particular theory of operation, Applicant believes that this is due to the fact that cultured β-cells are under heightened stress due to the high glucose concentration and the hyperoxia occurring in these culture conditions. The fusion protein protected these cells from this stress.

In summary, these studies showed that apoptosis can be prevented and cellular function enhanced by targeting specific repair proteins to mitochondria, and that these proteins can be delivered rapidly to mitochondria through protein transduction.

EXAMPLE 3

Figure 8:
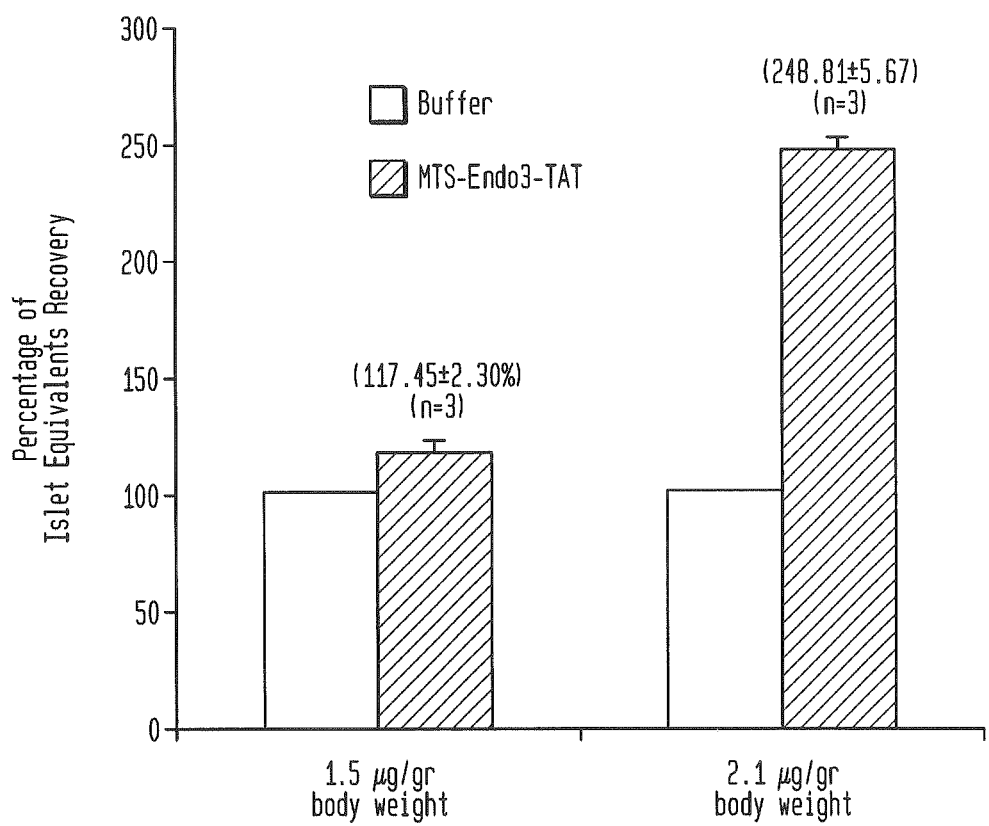
FIG. 8 is a bar graph showing the percentage of islet equivalents recovered as a function of varying doses of fusion protein from three separate experiments. To ascertain whether fusion proteins could be effective at protecting islets of Langerhans during the isolation procedure before transplantation, Rats were administered 1.5 or 2.1 μg/gram body weight of the fusion protein MTS-Endo III-TAT. Islets were recovered 24 hours later. The results in this figure show a significant enhancement in islet equivalents in islets isolated from rats receiving the fusion protein.
Figure 9:
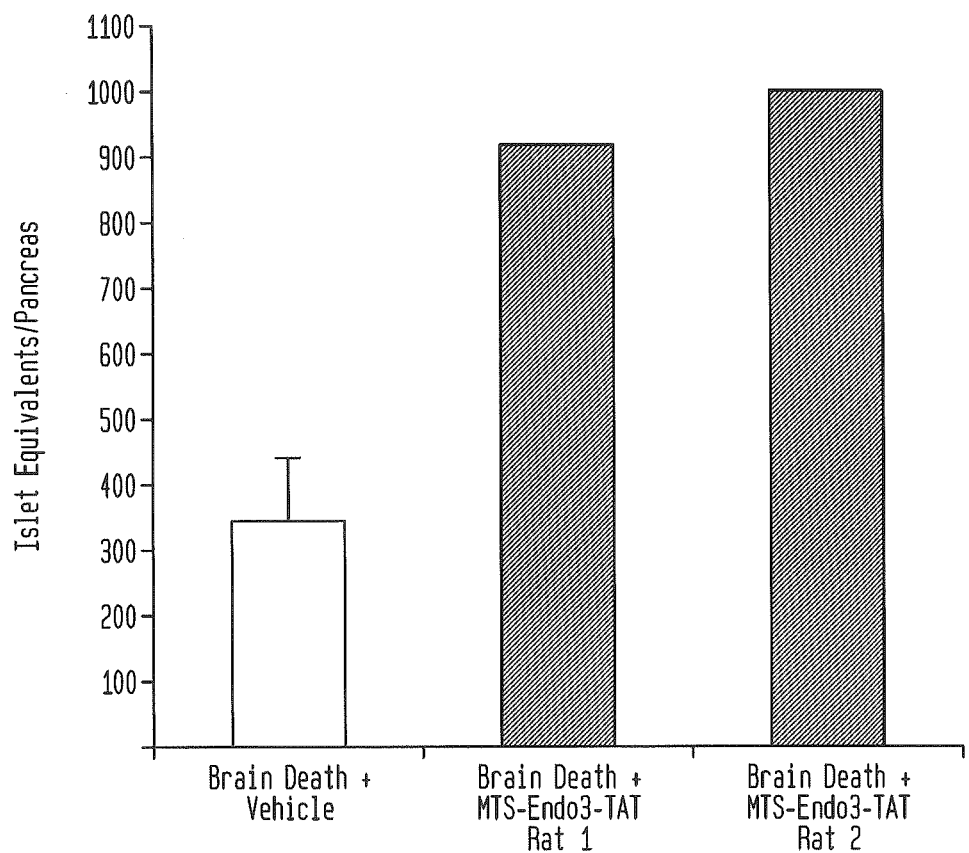
FIG. 9 is a bar graph showing islet equivalents/pancreas following ip injection of 1.5 μg/g body weight of MTS-Endo III-TAT, followed by induction of brain death and isolation of the islets. Because donors used for islet transplantation are brain dead and it has been shown that brain death causes loss of viability in transplanted tissues, Applicant evaluated whether a fusion protein could provide protection against the effects of brain death. As shown in this figure, there was over a doubling in the number of islets equivalents isolated from the brain dead animals receiving the fusion protein, compared to controls, both times that this experiment was performed.

A fusion protein was constructed to contain the mitochondrial transport sequence from MnSOD, the bacterial glycosylase/AP lyase Endonuclease III and the TAT sequence from HIV. See paragraphs [0053-56] herein. In the first set of experiments, the fusion protein was given to rats i.p. in two different doses and islets isolated the next day. Control animals received buffer only. Both concentrations significantly enhanced the recovery of islets with the higher concentration enhancing recovery by almost 250% (FIG. 8). To better simulate conditions during transplantation, the fusion protein was administered i.p. and rats were made brain dead via chemicals. Control animals received buffer only before induction of brain death. Two sets of animals have been done so far. In each case, twice as many islet equivalents were isolated from the rat treated with the fusion protein (FIG. 9).

Figure 10:
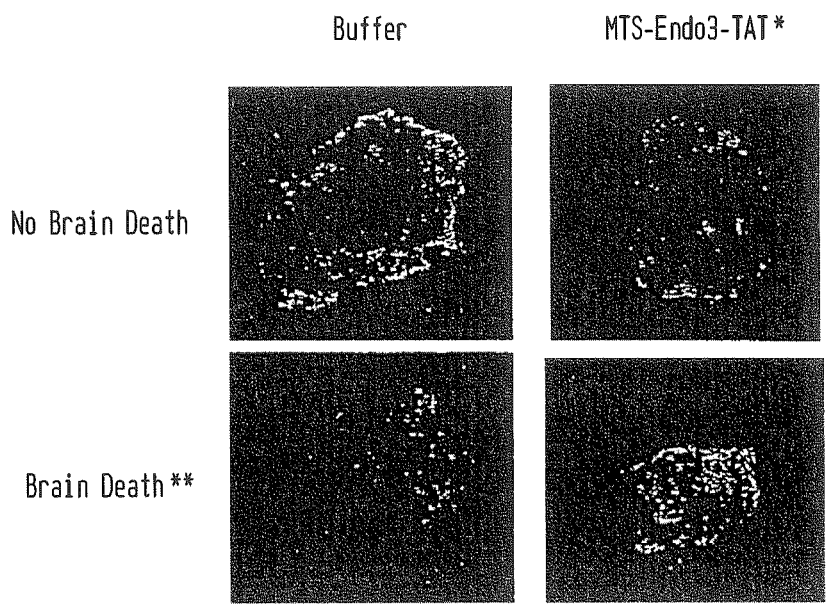
FIG. 10 displays photos of rat islets stained with ethidium bromide/acridine orange, isolated from normal and brain dead rats following i.p. injection of 1.5 μg/gram body weight of MTS-Endo III-TAT. Dead cells stain red and live cells stain green. As shown in this figure, there was a dramatic increase in the number of viable cells in the islets from the brain dead animals who received the fusion protein.

To determine the effect of the fusion protein on islet viability a double labeling technique was employed using ethidium bromide and acridine orange. Non-viable cells stain red while viable cells stain green. Representative islets are shown (FIG. 10) for animals with and without brain death treated with the fusion protein and controls with and without brain death treated with buffer. Viability in islets from animals receiving the protein without brain death was 95±2% compared to 87±3% in animals receiving buffer. In animals made brain dead, islet viability in rats treated with fusion protein was 85±5% while in brain dead animals receiving buffer it was 65±4%. Therefore, these data indicate that treatment with the fusion protein not only increases islet yield but also increases islet viability in both normal and brain dead animals.

EXAMPLE 4

Figure 11A:
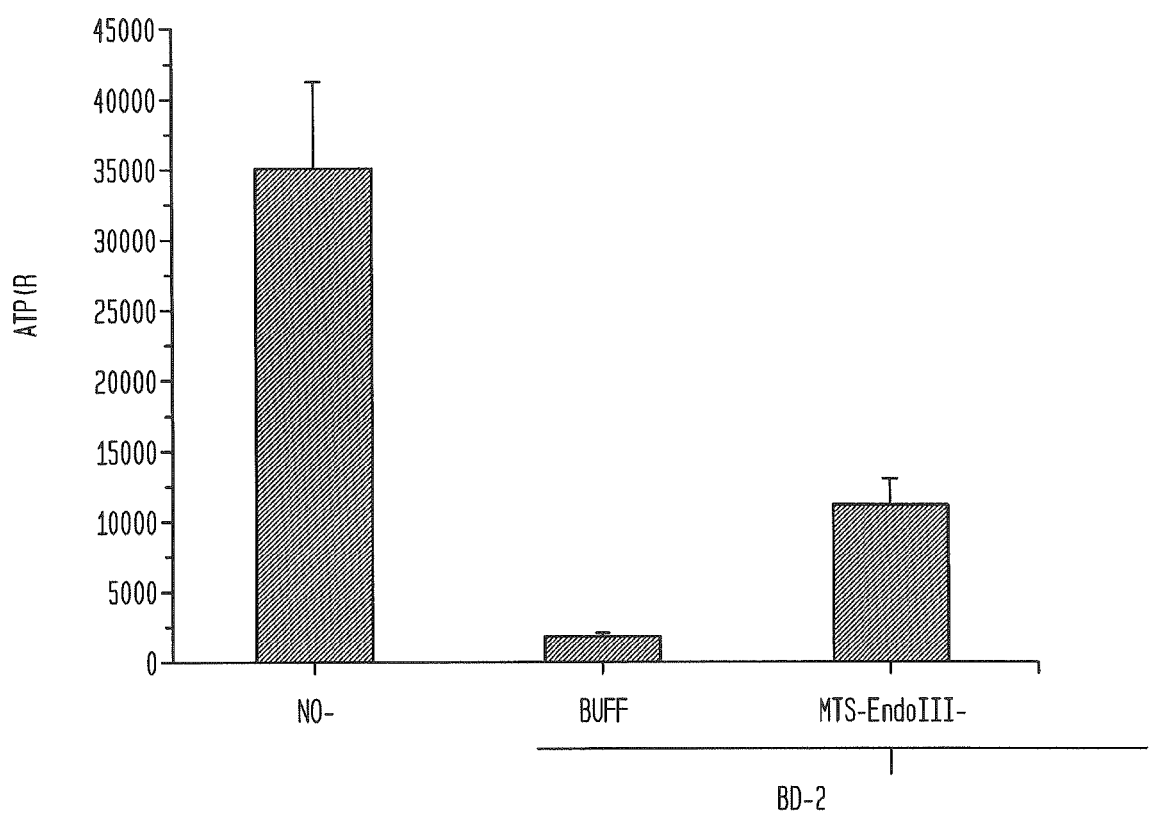
FIGS. 11A and B are bar graphs showing ATP levels in islets isolated from pancreata of rats which were injected with a fusion protein of the present invention versus controls.
Figure 11B:
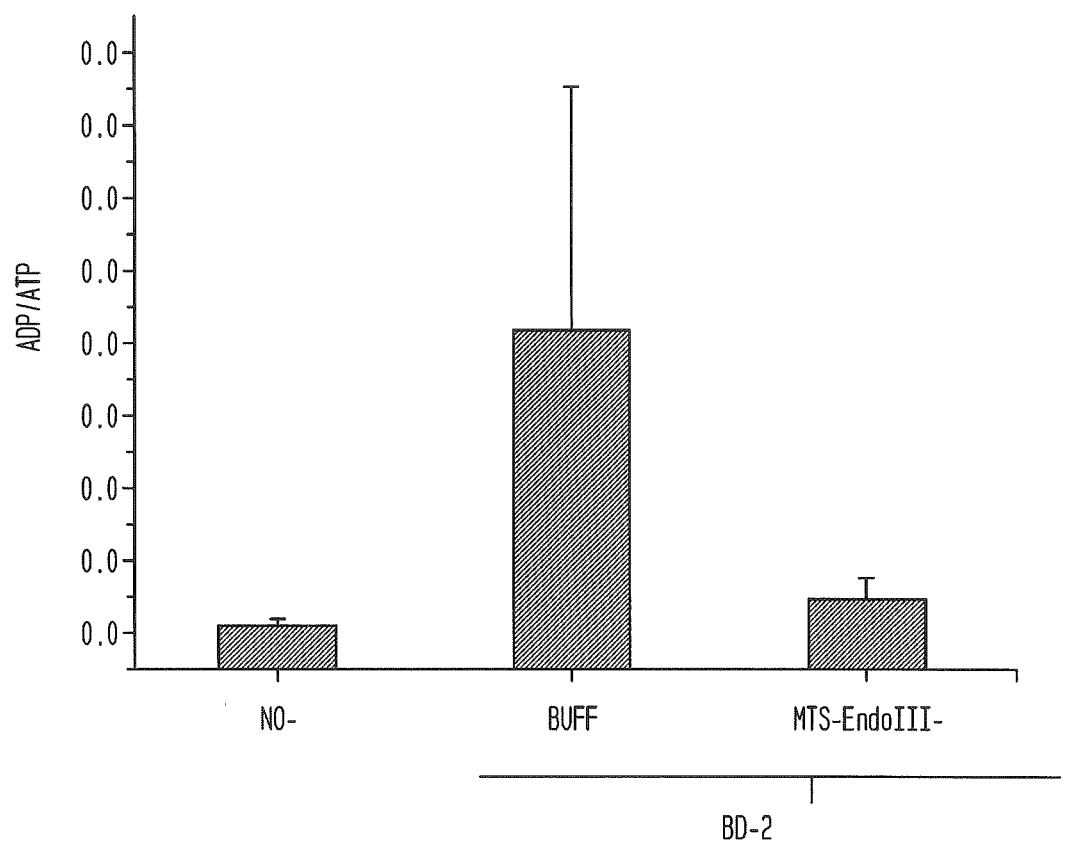

To evaluate whether the fusion protein from Example 3 is able to restore functional viability to islets, ADP/ATP ratios were evaluated in brain-dead rats. ATP is generated from ADP in mitochondria and serves as the energy molecule in the cell. Normal ADP/ATP ratios are an absolute requirement for insulin secretion. Three rats obtained from Charles River Mouse Farms were either given 1.5 μg/g body weight of fusion protein (described in Example 3) or glycerol-based dilution buffer and then made brain-dead. Two hours later, islets were isolated from the pancreata of these animals and evaluated for ATP and ADP levels. A second control group was comprised of animals which were not made brain-dead. The results which are illustrated in FIGS. 11A and B and show that islets from brain-dead animals which did not receive the fusion protein contained almost no ATP and thus had high ADP/ATP ratios. In marked contrast, islets from brain dead animals who had received the fusion protein contained significant amounts of ATP and had near normal ADP/ATP ratios, when compared with normal controls. These data show that the fusion protein containing the DNA repair enzyme was able to restore mitochondrial function in islets from brain-dead animals to near normal levels.

EXAMPLE 5

Treatment of Acute Lung Injury

This example demonstrates Use of a fusion protein construct (described in Example 3) to deliver DNA repair enzyme directly to mitochondria, and which protects against acute lung injury and pulmonary edema.

Figure 12:
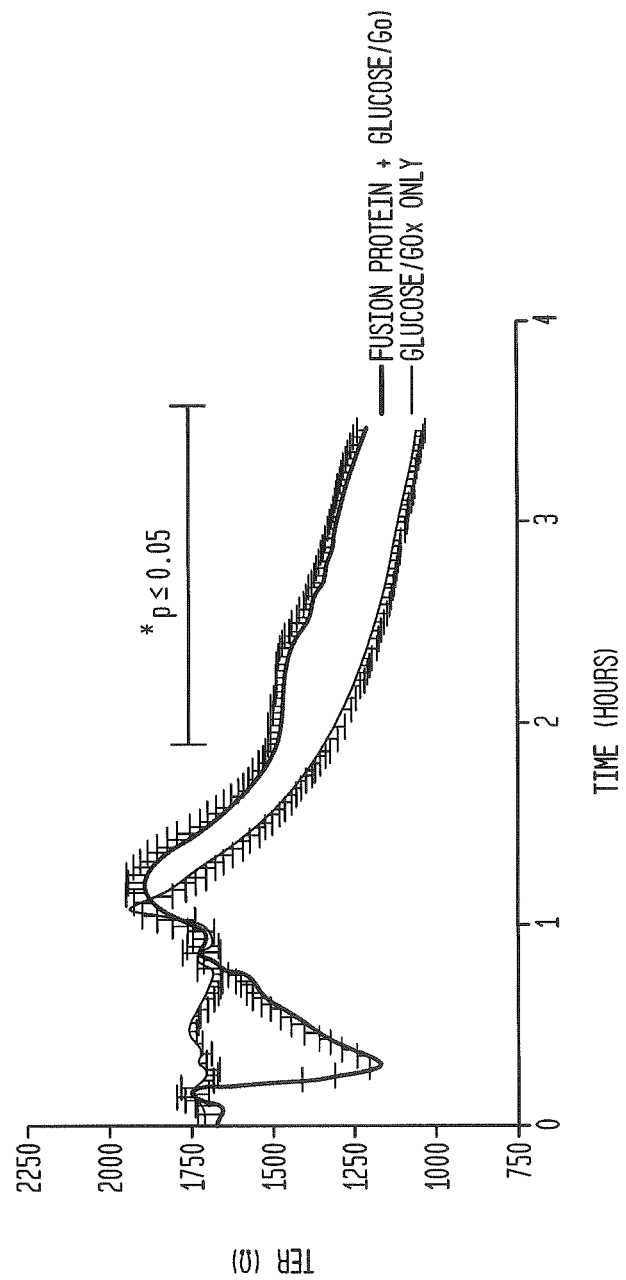
FIG. 12 is a graph showing impact of the fusion protein (FP) glucose oxidase (GOX)-glucose-induced changes in transendothelial electrical resistance in rat pulmonary microvascular endothelial cells. The presence of the fusion protein decreased the effect of GOX/glucose on transendothelial electrical resistance, thus indicating protection of endothelial cell barrier integrity.

First, rat pulmonary microvascular endothelial cells were cultured to confluency on gold plated microelectrodes, and Transendothelial Electrical Resistance across cell monolayers was measured using an electrical cell-substrate sensor (ECIS) system (Applied Biophysics, Troy, N.Y.) as an index of pulmonary endothelial permeability. Current was applied across the electrodes by a 4 kHz AC voltage source with amplitude of 1 mV in series with a 1 WM resistance to approximate a constant current source. The small gold electrode and larger counter-electrode (1 cm$^2$) were connected to a phase-sensitive lock-in amplifier (model 5301A, EG&G Instruments, Princeton, N.J.) with a built-in differential preamplifier (model 5316A EG&G Instruments). The phase-in and out-of-phase voltages between the electrodes were monitored in real time with the lock-in amplifier and converted to scalar measurements of transendothelial impedance of which resistances were the primary focus. In this system, addition of the hydrogen peroxide-generating enzyme, glucose oxidase, in the presence of glucose led to profound decreases in transendothelial electrical resistance. Importantly, and as shown in FIG. 12, pre-treatment of the cells with 20 microgram/ml fusion protein-DNA repair construct blunted by about 50% the decrease in transendothelial resistance, thus indicating that the fusion protein protects against barrier dysfunction in cultured lung microvascular endothelial cells.

Figure 13:
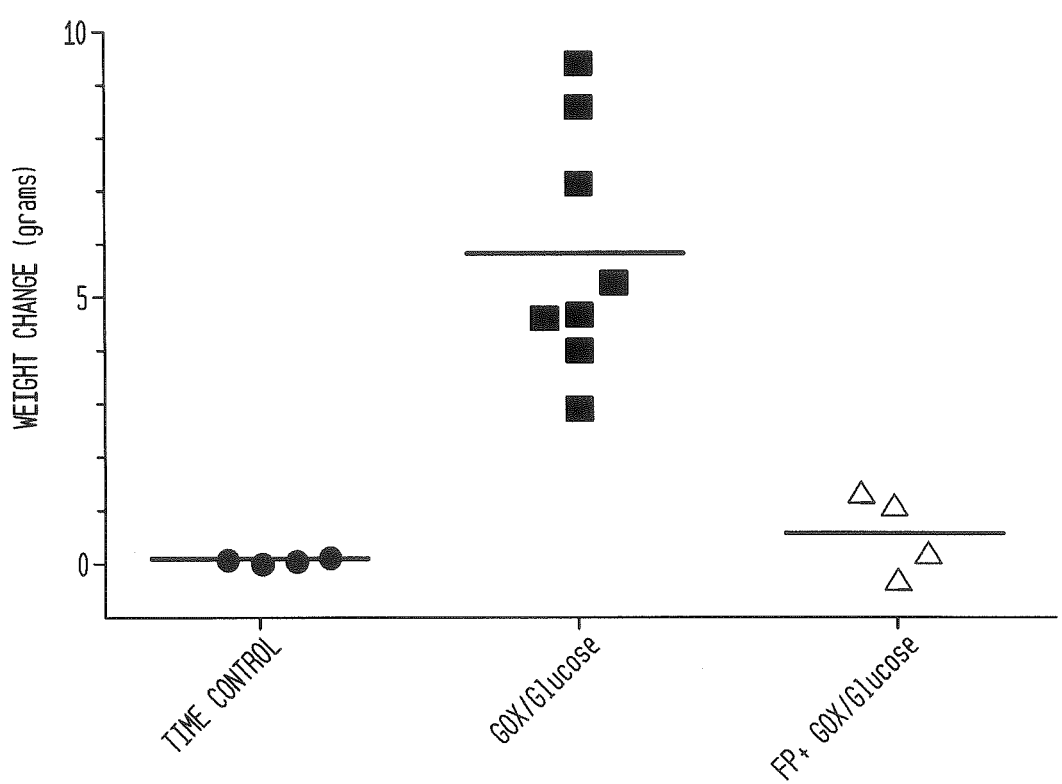
FIG. 13 is a graph showing impact of the fusion protein (FP) delivering DNA repair enzyme to mitochondria on pulmonary edema, assessed as change in lung weight, induced by glucose oxidase (GOX)-glucose in isolated perfused lungs. GOX/glucose failed to increase lung weight above time controls after pre-treatment with the fusion protein.

In companion studies, intact, buffer-perfused rat lungs were challenged with intravascular glucose oxidase-glucose solutions to engender hydrogen peroxide-induced endothelial injury, while increases in weight lung weight were monitored as a function of time as an index of pulmonary edema formation. This isolated lung preparation extends observations from cultured cells because it more closely mimics the behavior of the in vivo lung. As shown in FIG. 13, while glucose oxidase-generated hydrogen peroxide increased lung weight by 6 grams, pre-treatment with the fusion protein limited the increase to approximately 1 gram. These findings demonstrate that the fusion protein construct protects against acute lung injury.

EXAMPLE 6

BPD

Gestational day 15 rat fetuses were removed from timed-pregnant Sprague-dawley dams. Fetal hearts and lungs were removed enbloc, individual lung lobes were dissected from large airways and placed in culture on a transwell (Costar, USA). Lungs were cultured in a humidified chamber at the air-liquid interface for up to 72 hours at fetal oxygen tension (3% $O_2$ or 27 mmHg) or hyperoxia (21% $O_2$ or approx 140 mmHg). To test the capacity of the mtDNA repair fusion protein to repair fetal lung mtDNA and restore lung branching, the fusion protein construct (described in Example 3) was added to lung cultures (10, 25, 50 and 100 μg/ml). Lung branching was assessed grossly by counting terminal lung bud branch points (15 lobes/experiment N=5). Tissues were also harvested for biochemical analysis. The fusion protein restored lung branching in hyperoxic fetal lungs. As measured by quantitative Southern analysis, hyperoxia damages mitochondrial DNA in the fetal lung, the fusion protein designed to facilitate repair of mitochondrial oxidative damage was found to restore mtDNA integrity as well as fetal lung branching in the hyperoxia exposed tissues.

All publications cited in the specification, including patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A multi-domain conjugate comprising, from N-terminus to C-terminus, a mitochondrial targeting sequence, a DNA repair enzyme comprising human 8-oxoguanine DNA glycosylase (hOGG1) or Endo III (Endonuclease III), and a protein transduction domain.

2. The multi-domain conjugate of claim 1, wherein the DNA repair enzyme comprises human 8-oxoguanine DNA glycosylase (hOGG1).

3. The multi-domain conjugate of claim 1, wherein the DNA repair enzyme comprises Endo III.

4. A composition for inhibiting damage to mitochondrial DNA, comprising a therapeutically effective amount of the multi-domain conjugate of claim 1, and a pharmaceutically acceptable carrier.

5. The composition of claim 4, wherein the carrier comprises water.

6. The composition of claim 4, wherein the carrier comprises saline.

7. The composition of claim 4, wherein the carrier comprises a buffer.

8. A method of treating oxidative-stress induced damage to mitochondrial DNA, comprising administering to a patient in need thereof, a therapeutically effective amount of the multi-domain conjugate of claim 1.

9. The method of claim 8, wherein the patient has Crohn's disease.

10. The method of claim 8, wherein the patient has ulcerative colitis.

11. The method of claim 8, wherein the patient has ischemic heart disease.

12. The method of claim 11, wherein the patient is an obese pre-diabetic.

13. The method of claim 11, wherein the patient is diabetic.

14. The method of claim 13, wherein the patient has type II diabetes.

15. The method of claim 8, wherein the patient has acute lung injury or acute respiratory distress syndrome.

16. The method of claim 15, wherein the acute lung injury is bronchopulmonary dysplasia.

17. The method of claim 16, wherein the patient is an infant.

18. The method of claim 8, wherein the patient has radiation induced-brain injury.

19. A method of enhancing viability of islets of Langerhans which comprise β-cells for purposes of transplantation, comprising contacting the islets of Langerhans with a therapeutically effective amount of the multi-domain conjugate of claim 1.

20. A multi-domain conjugate comprising, from N-terminus to C-terminus, a mitochondrial targeting sequence, wherein the mitochrondrial targeting sequence is MLFNLRILLNNAFRNGHNFMVRNFRCGQPLQ (SEQ ID NO:4), a DNA repair enzyme comprising human 8-oxoguanine DNA glycosylase (hOGG1) or Endo III (Endonuclease III), and a protein transduction domain.

21. A multi-domain conjugate comprising, from N-terminus to C-terminus, a mitochondrial targeting sequence, a DNA repair enzyme comprising human 8-oxoguanine DNA glycosylase (hOGG1) or Endo III (Endonuclease III), and a protein transduction domain, wherein the protein transduction domain is RQIKIWFQNRRMKWKK (SEQ ID NO:10).

* * * * *